United States Patent [19]
Chishti

[11] Patent Number: 5,401,835
[45] Date of Patent: Mar. 28, 1995

[54] HUMAN ERYTHROID P55 NUCLEIC ACIDS

[76] Inventor: Athar H. Chishti, 131 Sewall Ave., Unit 56, Brookline, Mass. 02146

[21] Appl. No.: 923,739

[22] Filed: Jul. 31, 1992

[51] Int. Cl.$^6$ .................... C07H 21/02; C07H 21/04
[52] U.S. Cl. .................. 536/23.2; 536/23.5; 536/24.35; 435/6
[58] Field of Search ............... 435/6; 536/23.2, 24.31, 536/23.5

[56] References Cited

FOREIGN PATENT DOCUMENTS 274560A 7/1988 European Pat. Off. .

OTHER PUBLICATIONS

Ruff et al., *Proc. Natl. Acad. Sci. U.S.A.*, 88:6595–6599 (1991) (Aug.).
Adams, M. D. et al., "Sequence Identification of 2,375 Human Brain Genes", *Nature* 355:632–634 (1992).
Woods, D. F. et al., "dlg-R Proteins: Modified Guanylate Kinases", *Nature Genet.* 256–257 (1993).
Chishti, A. et al., "Human Erythroid P55: Homolog of Drosophila Tumor Suppressor Factor is Highly Conserved X-Linked Gene Product with Guanylate Kinase Activity", *Blood* 80(10):586 (1992).
Bryant, P. J. et al., "A Major Palmitoylated Membrane Protein of Human Erythrocytes Shows Homolog to Yeast Guanylate Kinase and to the Product of a Drosophila Tumor Suppressor Gene", *Cell* 68:621–622 (1992).
Goebl, M. G. et al., "Is the Erythrocyte Protein p55 a Membrane-Bound Guanylate Kinase", *TIBS* 17 (1992).
Cho, K. O. et al., "The Rat Brain Postsynaptic Density Fraction Contains a Homolog of the Drosophila Discs-Large Tumor Suppressor Protein", *Neuron* 9:929–942 (1992).
Metzenberg, A. B. et al., "The Gene Encoding the Palmitoylated Erythrocyte Membrane Protein, p55, Originates at the CpG Island 3' to the Factor VII Gene", *Human Molec. Genet.* 1(2):97–101 (1992).
Das, A. K. et al., "Fatty Acylation of a 55 kDa Membrane Protein of Human Erythrocytes", *Biochem. Biophy. Acta* 1108:128–132 (1992).
Woods, D. F. et al., "The Discs-Large Tumor Suppressor Gene of Drosophila Encodes a Guanylate Kinase Homolog Localized at Septate Junctions", *Cell* 66:451–464 (1991).
Chishti, A. et al., "Purification of Erythrocyte Dematin (Protein 4.9) Reveals in an Endogenous Protein Kinase that Modulates Actin-Bunding Activity", *J. Biol. Chem.* 264(15):8985–8991 (1989).
Chishti, A. et al., "Abolition of Actin-Bundling by Phosphorylation of Human Erythrocyte Protein 4.9", *Nature* 334(6184):718–721 (1988).

*Primary Examiner*—Margaret Parr
*Assistant Examiner*—Kenneth R. Horlick
*Attorney, Agent, or Firm*—Harness, Dickey & Pierce

[57] ABSTRACT

Human erythroid p55, an abundantly palmitoylated erythrocyte membrane protein, has been identified, cloned and sequenced. p55 appears to be ubiquitously expressed in human tissues and contains both an SH3 motif and an enzymatically active guanylate kinase domain. The presence of the SH3 motif indicates a possible role in the suppression of tyrosine kinase activity and the guanylate kinase domain may play a role in signal transduction and tissue proliferation by modulating guanine nucleotide levels. Localized to the Xq24-qter region of the X chromosome, abnormalities in p55 appear in patients suffering from hemolytic anemia and Dyskeratosis congenita. With the identification and sequencing of p55, nucleic acid probes and anti-p55 antibodies can be used in a variety of hybridization and immunological assays to screen for and detect p55 defects. Conventional and gene techniques can also be developed to treat p55 deficiencies and abnormalities.

11 Claims, 15 Drawing Sheets

```
p55        AqFDYDPKkDNlipckEagLkFatGD-IIQIIN-KDDSnWWqG-R-V-EGssKE-SaGLIPSP-eL
c-src      slyDYksr-D------EsdLsFmkGD-rmevI-ddteSdWW---R-V-vnlttrqe-GLIPln-fv  33%
v-crk      AlFDf--K-gN------ddgdLpFkkGD-IlkIr-dKpeeqWWnaed-m-dG--K-r--GmIPvP-yv  34%
v-yes      AlyDYearttd------d--LsFkkGe-rfQIIN-ntegdWWea-Rsi-atg-K-t--GyIPSn-yv  31%
α-sp       AlyDYqeK---s--P-rEvtmk--kGD-IItIIN-stnkdWW---k-V-Evndrq---GfvPaa-yv  29%
myo1b      AlFDYfaa-eN--P-dE--LtFneGa-vvtvIN-Ksnpd WWeG-e-l-nG--q-r--GvfPas-yv  32%
myo1l      AlyDYDaqtgd-----E--LtFkeGD-tI-IvhqKDpagWWeG-e-l-nG--K-r--GwvPan-yv  35%
abp1       AeyDYDaaeDN------E--LtFvenDkIInIefv-DD-dWWlG-el--E---KdgSkGLfPSn-yv  41%
cac-βs     tnvgYnPspgdevPvegvaitFepkDf-lhIke-KynndWWiG-RlVkEGc--E-v-GfIPSPvkL  34%
plc-γ      AlFDYkaqred-----E--LtFtksa-IIQnve-KqeggWWrgd-y-h--hkKq---lwfPSn-yv  31% consensus  A FDYDPK DN    P  E  LF    D  IQIIN KDDS WW G R V EG   KE S GLIPSP  L
```

Figure 3

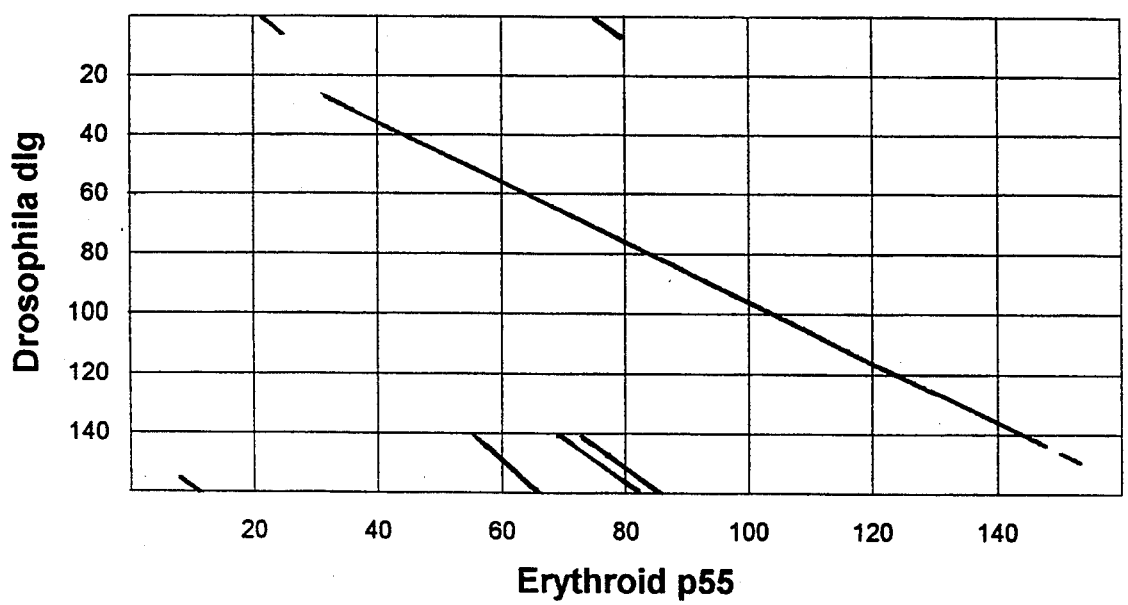
Figure 6B1
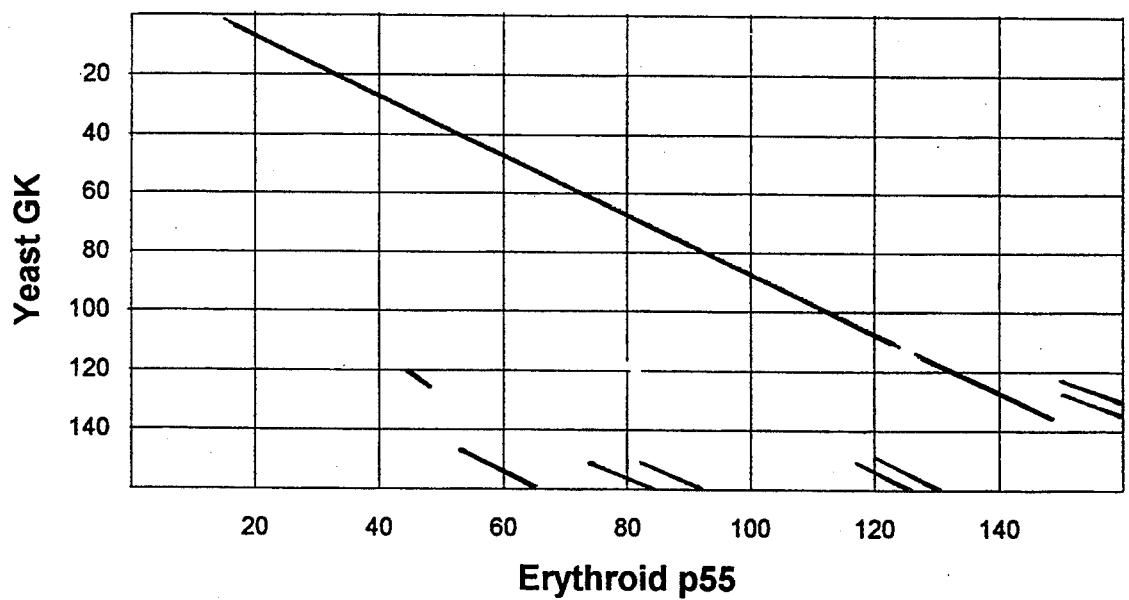
Figure 6B2

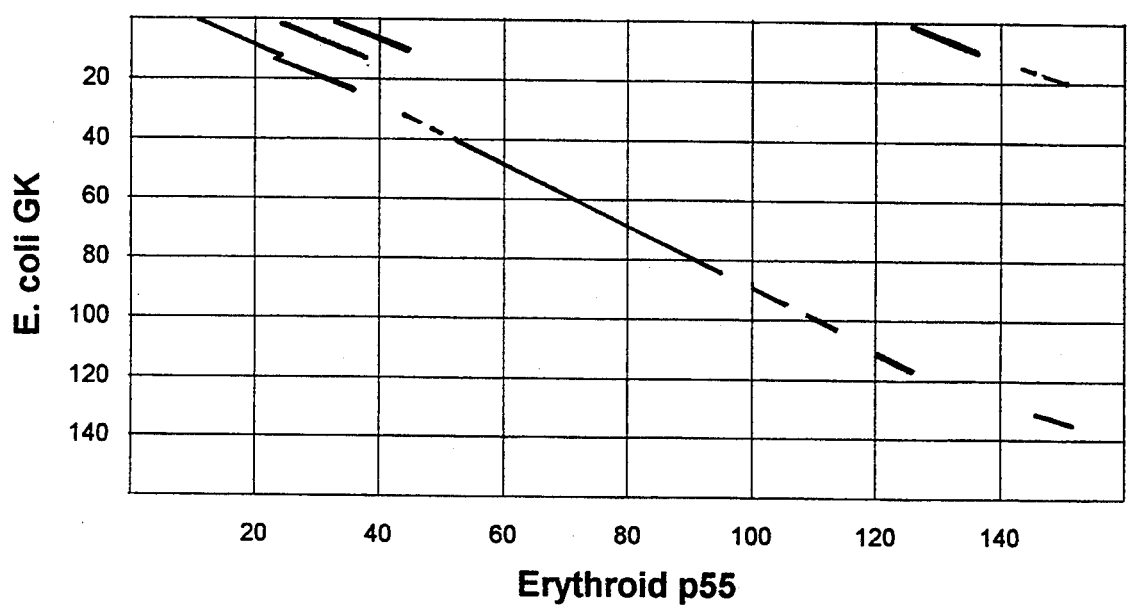
Figure 6B3

HUMAN ERYTHROID P55 NUCLEIC ACIDS

GENBANK DEPOSIT

The cDNA sequence and deduced amino acid sequence have been deposited in the GenBank database with later corrections and accorded Accession No. M64925.

FIELD OF THE INVENTION

The present invention relates generally to human erythroid p55, an abundantly palmitoylated erythrocyte membrane protein with a SH3 motif and an enzymatically active guanylate kinase domain. More specifically, the invention relates to the cloning and sequencing of p55, its use as a research and screening tool, and its clinical applications as a diagnostic and therapeutic agent.

BACKGROUND OF THE INVENTION

Human erythroid p55 of the present invention was originally identified as a 55 kDa phosphoprotein that copurified with preparations of dematin, an actin-bundling protein of human erythrocyte membranes (1–3). Although fractions enriched with the 55 kDa protein completely inhibited dematin's actin-bundling activity, this inhibitory activity was traced to the presence of a protein kinase distinct from the 55 kDa protein (1–3).

Lacking any protein kinase function, independent interaction with actin, or any other known function, the 55 kDa protein was no longer of interest with respect to actin-bundling activity in erythrocytes. However, the subsequent molecular cloning and sequencing of human erythroid p55 in accordance with the present invention revealed the unexpected presence of the src homology 3 (SH3) motif conserved in regulatory domains of the non-receptor class of oncogene-encoded tyrosine kinases (4–6, 43–44). Further characterization of human erythroid p55 in accordance with the invention surprisingly revealed that the C-terminal half of p55 also contains an enzymatically active guanylate kinase domain with significant homology to guanylate kinases of yeast and E. coli.

The importance of the SH3 motif is underscored by mutational studies which indicate that the SH3 motif may play a role in the suppression of tyrosine kinase activity in vivo and may participate in the process of tumor suppression (14–16). For example, mutations in the N-terminal SH3-containing regions of the srs and abl gene products are known to activate their oncogenic potential (14,15). The neuronal src gene product, which has enhanced tyrosine kinase activity, contains a hexapeptide insert in the SH3 motif (16). Suppressive activity of the SH3 sequence is further evidenced by the inhibition of tyrosine kinase activity of the v-src product in vitro by a synthetic peptide corresponding to part of the SH3 motif (17).

The presence of the SH3 motif in a diverse group of cytoskeletal and signal-transducing proteins unrelated to tyrosine kinase supports the hypothesis that it may mediate binding to regulatory ligand(s) common to these proteins (6). Such a ligand may block the transforming ability of various oncogene-encoded tyrosine kinases (15). Alternatively, the SH3 motif may mediate recognition of substrate molecules and regulate their proximity to the plasma membrane.

The amino acid sequence of p55, including both SH3 and guanylate kinase domains, as well as an N-terminal undefined domain, is also very similar to the primary sequence of the Drosophila tumor suppressor gene product dlg. It was recently demonstrated that recessive lethal mutations of the Drosophila dlg locus produced neoplastic overgrowth in imaginal discs (45). More specifically, such mutations caused a loss in apical-basal cell polarity and induced proliferation of epithelial tissues (45). These studies predict that the guanylate kinase domain of p55 may influence signal transduction and tissue proliferation by modulating guanine nucleotide levels at the plasma membrane (45).

The sequencing and characterization of human erythroid p55, and its use in research and clinical applications, thus provide various aspects of the present invention described more fully below.

SUMMARY OF THE INVENTION

Human erythroid p55, an abundantly palmitoylated erythrocyte membrane protein with peripheral membrane protein characteristics, has been identified, cloned and sequenced, and is set forth in the Sequence Listing. Thus one aspect of the present invention comprises the nucleic and amino acid sequences substantially as shown in SEQ ID NOS. 1 and 2, segments thereof and methods of their use. By "substantially as shown" (or "substantially similar") is meant that any variation therefrom does not impair the desired functionality of the sequence to any significant degree. Sequences of the present invention include sequences isolated from in vivo and in vitro sources, as well as those synthesized in vitro and ex vivo.

p55 contains an SH3 motif and an enzymatically active guanylate kinase domain, a domain never before reported in a peripheral membrane protein. Erythroid p55 and its isoforms may thus define a new family of peripheral membrane proteins that regulate levels of guanine nucleotides at the plasma membrane and thus may influence cellular signals which modulate signal transduction and tissue proliferation.

The primary structure of erythroid p55 does not predict any transmembrane domain and its membrane-association properties are consistent with its classification as a peripheral membrane protein. Its tight association with the plasma membrane is, however, reminiscent of an integral membrane protein. This may be partly explained by the fact that p55 appears to be the most extensively palmitoylated protein of the erythrocyte membrane (24, 39, 43).

Stoichiometrically, p55 is a significant component of human erythrocyte membranes with approximately 80,000 copies per cell (43). p55 is distributed ubiquitously in human tissues and is widely conserved in various animal species. While its precise physiological function remains to be elucidated, the p55 gene has been localized to the q24-qter region of the X chromosome containing loci for a number of severe hereditary disorders.

With the identification, cloning and sequencing of p55, nucleic acid probes and antibodies raised to p55 are used within the scope of the invention in a variety of hybridization and immunological assays to screen for the presence or abnormalities of the p55 gene, transcript or product. Assays which measure levels of gene function can also been employed for diagnosis or to monitor treatment. Assay kits for such screening and diagnosis in accordance with the principles of the invention can also be provided.

Treatment of p55 abnormalities, now implicated in diseases such as hemolytic anemia and Dyskeratosis congenita, through supplementation with p55 or its functional equivalent, is now feasible. Conventional therapeutic approaches can also be utilized. In addition, disease states resulting from a defect in p55 may be cured or controlled through gene therapy by correcting the gene defect in situ or using recombinant or other vehicles to deliver DNA sequences capable of expression of the normal gene product.

Other features and advantages of the present invention will become apparent from the following description and appended claims, taken in conjunction with the accompanying drawings.

BRIEF DESCRIPTION OF THE FIGURES

FIG. 3 depicts the alignment of SH3 amino acid sequences (single-letter code). From the top: p55, p60$^{c\text{-}src}$, p47$^{gag\text{-}crk}$, p90$^{v\text{-}yes}$, α-10 domain of Drosophila spectrin, Acanthamoeba myosin 1B and 1L, yeast actin-binding protein, β subunit of skeletal muscle calcium channel, and phospholipase C-γ. The percent identity between the SH3 motif in p55 and the SH3 motif in each protein is indicated at right.

FIG. 6(B) is a dot matrix alignment of the guanylate kinase domain of erythroid p55 with the guanylate kinase domains in dlg (45) yeast (55) and E. coil (GenBank Accession No. P24234). No repeat structure was observed within guanylate kinase domains. Comparison was carried out by MacVector program from IBI, New Haven, Conn., using parameters: window size 25, minimum % score 20, hash value 1. The scoring matrix was pam 250.

FIG. 7(A) results illustrate that production of [$^{32}$P]GDP from GMP was detected only in presence of purified p55.

With FIGS. 8(A) and (B) are Northern blot analyses illustrating the ubiquitous nature of p55 transcript.

FIG. 12 is a Western blot analysis of p55 in hereditary hemolytic anemia patients.

DETAILED DESCRIPTION OF THE PREFERRED EMBODIMENTS

A. SPECIFIC EXAMPLES—GROUP I

Materials and Methods

Figure 1:
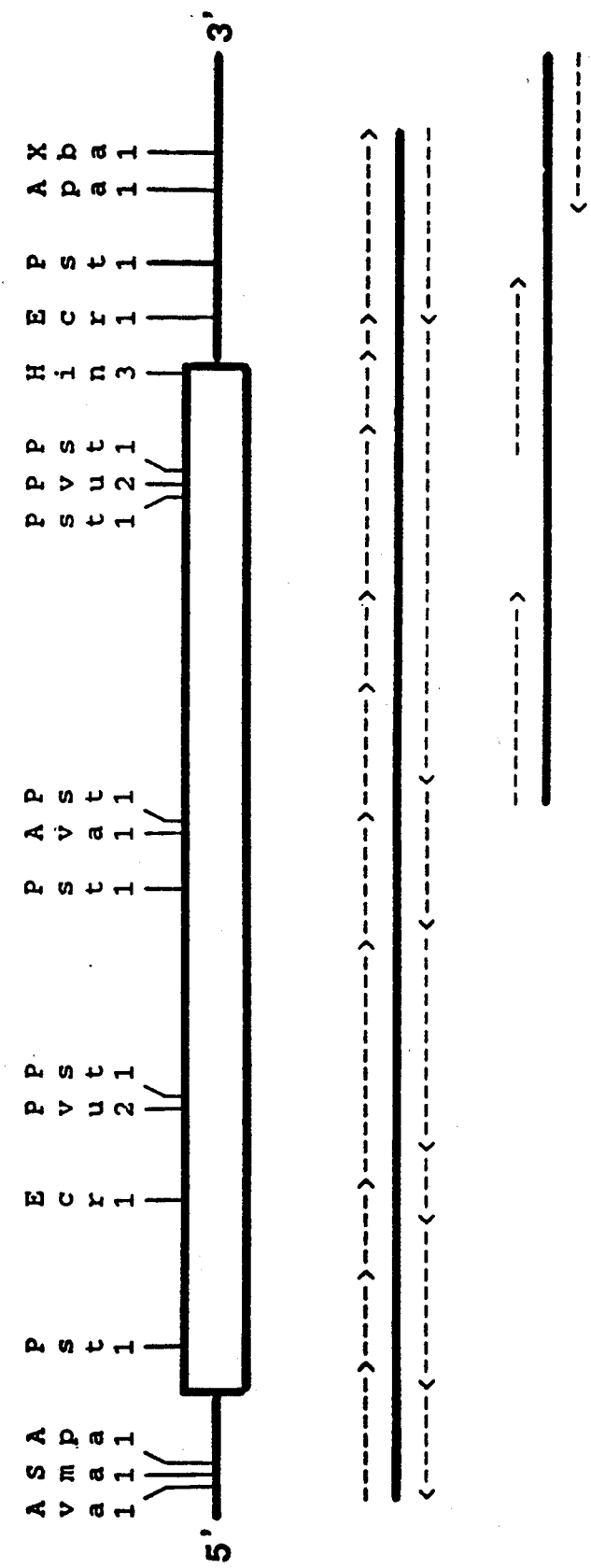
FIG. 1 illustrates the organization of human erythrocyte p55 cDNA. The restriction map was obtained from two overlapping clones extending a total of 2.0 kb from a human reticulocyte λgt11 cDNA library. The central block (nucleotides 115-1512) represents the coding region. Both strands were sequenced, and dashed arrows indicate the sequencing strategy. Ecr1: EcoRI; Hin3: HindIII.

A human reticulocyte λgt11 cDNA library (a gift from J. Conboy, University of California, San Francisco) was screened using rabbit polyclonal antibodies against purified native p55 (18). Positive plaques were purified and phage DNA was analyzed by EcoRI digestion (19). Agarose gel-purified, EcoRI-digested inserts were subcloned into the plasmid pGEM-4Z (Promega) and sequenced by the dideoxynucleotide method (20). Further clones were isolated from the library by using a central 1.1 kilobase (kb) fragment as probe. The probe was labeled with [α-$^{32}$P]dCTP by using a random primer kit (Amersham). Nucleotide and deduced amino acid sequences were analyzed by computer software from Dnastar (Madison, Wis.).

Total RNA was isolated from peripheral blood from subjects with idiopathic hemochromatosis by a method that involves selective lysis of leukocytes (21). RNA obtained by this method is free of RNA from contaminating leukocytes (21). RNA was fractionated in 2.2M formaldehyde/1.4% agarose gels and blotted onto nitrocellulose (19). Northern blots were hybridized and washed under stringent conditions prior to autoradiography for 72 hr at −70° C. (19).

Solubilization and extraction studies of human erythrocyte plasma membrane were carried out as described (22). The copy number of p55 was determined by a quantitative immunoblot assay similar to the one developed for synapsin (23). Palmitoylation of intact erythrocytes was carried out as described (24). However, fresh erythrocytes were not depleted of endogenous fatty acids and were immediately incubated with [$^3$H] palmitate at 37° C. SDS/PAGE and immunoprecipitations were carried out by established methods (25).

Results

DNA Cloning and Sequencing

FIG. 1 shows cDNA clones encoding the complete amino acid sequence of p55. Both strands were sequenced as shown. The following amino acid residues were also confirmed by automated gas-phase sequencing of seven peptides produced by *Staphylococcus aureus* V8 protease and one peptide (residues 227–236) produced by cleavage with 3-bromo-2-(2'-nitrophenylsulfenyl) skatole: 8–24, 21 4–222, 227–236, 331–338, 339–347, 351–364, 411–420 and 442–448. Amino acid residues 165–233 represent the SH-3 motif.

The initiator codon begins 115 base pairs (bp) from the 5' end and reveals an open reading frame of 1398 bp (SEQ ID NO. 1). Evidence that this ATG codon is the initiator includes: (i) the presence of a purine 3 bp upstream (26); (ii) the match of a peptide sequence produced by S. aureus V8 protease cleavage of p55 with the predicted sequence from amino acids 8–24; and (iii) the lack of any downstream methionine that could account for the complete amino acid sequence (SEQ ID NOS. 1 and 2). A single cDNA clone was isolated that contained the entire open reading frame, coding for a 466-amino acid protein of 52.9 kDa with an isoelectric point of 7.0. The stop codon is followed by an untranslated region of 488 bp with a consensus polyadenylylation sequence AATAAA at nucleic acids 1982–1987 (SEQ ID NO. 1). The size of the total cDNA (2 kb) is consistent with the size of the message from human reticulocytes (SEQ ID NO. 2).

Several lines of evidence show that the cDNA encodes an authentic p55: (i) polyclonal antibodies affinity-purified against p55 recognized fusion proteins encoded by the cDNA; (ii) purified p55 and the fusion protein produced similar one-dimensional CNBr peptide maps (not shown); and (iii) amino acid sequences of eight different peptides derived from purified p55 were identical to the predicted amino acid sequence in SEQ ID NO. 2. A hydropathy plot of the deduced amino acid sequence (27) revealed a predominantly hydrophilic character. Analysis of the secondary structure with the Chou-Fashman algorithm (28) showed a predominance of β-sheets with little α-helical content (data not shown). These results suggest that p55 is a globular protein with no transmembrane component, a property consistent with a peripheral membrane protein.

Northern analysis

Figure 2:
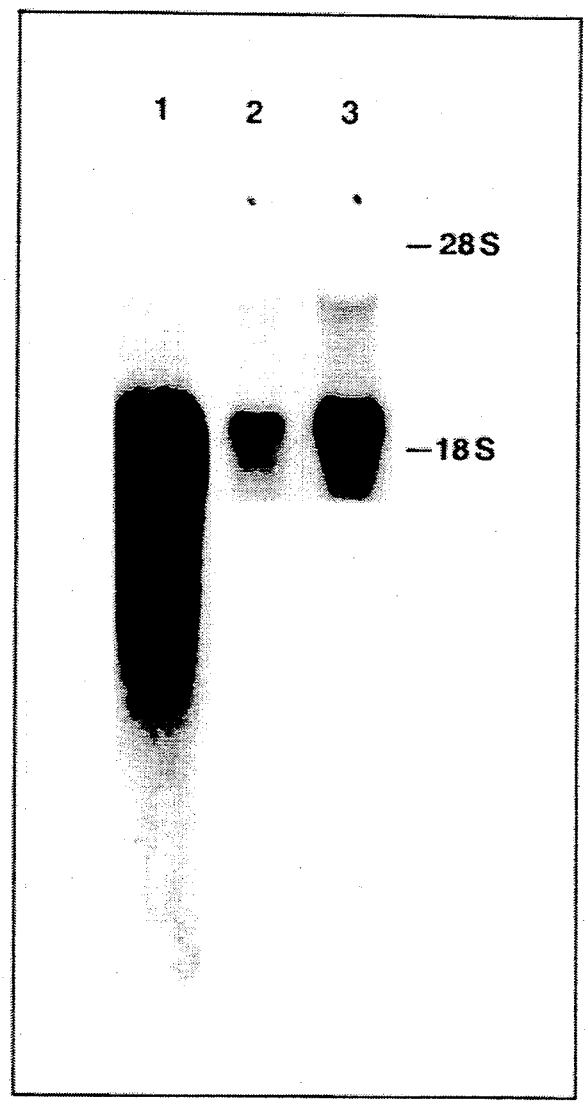
FIG. 2 is a Northern blot analysis of total RNA from human reticulocytes and K562 cells. Blots were probed with radiolabeled 1.1 kb fragment of p55 cDNA. Lane 1: total RNA (30 μg) from reticulocytes (a single message of 2.0 kb was detected); lane 2: total RNA (20 μg) from uninduced K562 cells; lane 3: total RNA (20 μg) (transcripts of 2 and 4 kb were detected) from K562 cells induced for 6 hr with 1-β-D-arabinofuranosylcytosine (ara-C). Positions of 28S and 18S rRNA are shown at right.

The mRNA of p55 is one of the most abundant messages in human reticulocytes. A comparative Northern blot assay using cDNA probes for p55, band 3, ankyrin, spectrin, proteins 4.1 and 4.2, and chicken erythrocyte dematin suggested that p55 and protein 4.1 mRNAs are among the most abundant messages in human reticulocytes (data not shown). Although protein 4.1 is synthesized late during erythropoiesis (29), p55 appears to be constitutively expressed throughout erythropoiesis (FIG. 2). Northern blot analysis of total RNA from K562 cells, a multipotent hematopoietic precursor cell line, showed a 2.0 kb p55 message (FIG. 2, lane 2). After induction with ara-C, which commits K562 cells to terminal erythroid differentiation (30), a 2-fold amplification of p55 message was observed (FIG. 3, lane 3). A faint 4.0 kb message was also detected and underwent amplification with ara-C. Although the origin of the 4.0 kb message is not known, it may arise from alternative splicing.

Homology with Oncogene-Encoded Tyrosine Kinases and Other Membrane Proteins

A computer search of the Swiss-Prot database (release no. 17)(31) revealed identities of up to 41% between a 59-amino acid region of p55 (residues 165–233, SEQ ID NO. 2) and the SH3 domains in the noncatalytic region of non-receptor tyrosine kinases (FIG. 3). This family of tyrosine kinase genes, of which the protooncogene c-src is the prototype, includes lyn, syn, hck, yes, blk, lck, fgr, and abl (7,8), as well as v-crk, a transforming oncogene whose product lacks tyrosine kinase activity (32). The SH3 motif has also been found in proteins that associate with the cytoskeleton and play diverse roles in signal transduction (6): a yeast actin-binding protein (7), phospholipase C-γ (8), myosin 1 (9,10), erythroid and nonerythroid α-spectrins (33–35), calcium-channel β subunit (11), neutrophil oxidase factor (12), and GTPase-activating protein (13).

Association of p55 with the Erythrocyte Plasma Membrane

Figure 4A:
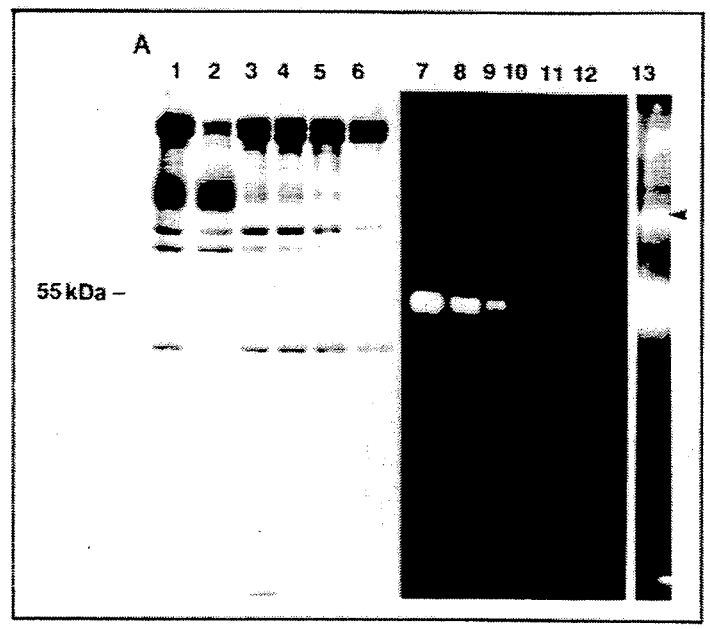
FIG. 4(A) is an SDS/PAGE analysis of solubilized erythrocyte membrane p55. Erythrocyte membrane "ghosts" were incubated in solubilization buffers on ice for 60 min. After centrifugation at 35,000 rpm (type 42.2 Ti rotor) for 60 min. supernatant was removed and pellets were analyzed by SDS/10% PAGE. Lane 1: ghosts; lane 2: IOVs; lane 3: Triton-extracted ghosts; lane 4: Triton plus 50 mM KCl; lane 5: Triton plus 150 mM KCl; lane 6: Triton plus 500 mM KCl. Buffer contained 0.5% Triton X-100, 50 mM Tris-HCl (pH 7.5), 1 mM EDTA, 1 mM EGTA and a mixture of NaF, vanadate, ouabain, and protease inhibitors. Lanes 1-6 are Coomassie-stained and lanes 7-12 are corresponding immunoblots with p55 polyclonal antibodies. Lane 13 represents a longer exposure of lane 7, indicating a higher molecular weight form of p55 (arrowhead). Note that p55 was completely solubilized in isotonic Triton solution (lane 11).
Figure 4B:
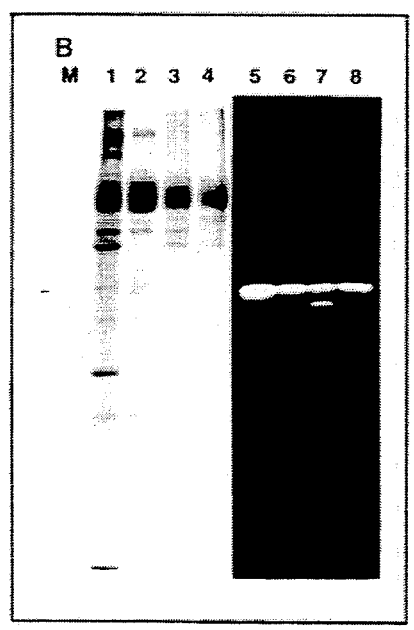
FIG. 4(B) is an SDS/PAGE analysis of p55 extractions from IOVs (inside out vesicles). Lane M: purified p55; lane 1: IOVs; lane 2: IOVs plus 0.1 mM EGTA (pH 11.0 at 23° C.); lane 3: IOVs plus 1M KCl (at 37° C.); lane 4: IOVs plus 1M Kl plus 0.5 mM EGTA (pH 8.0 at 23° C.). Samples were incubated for 60 min and centrifuged as described above. Lanes 1-4 are Coomassie-stained and lanes 5-8 are corresponding immunoblots. Note that a fraction of p55 (25%) was resistant to all extraction conditions in the absence of Triton X-100. Lane 7 shows partial proteolysis of p55 in the presence of 1M KCl.

Although p55 has not been studied before, some information may be obtained from studies of dematin (1–3). p55 does not associate with F-actin in sedimentation assays and does not appear to bind to dematin with high affinity since the two proteins can be separated on anion-exchange columns (2). Gel filtration failed to detect any interaction between p55 and human erythrocyte spectrin (data not shown). p55 remained associated with erythrocyte inside-out vesicles (IOVs) after removal of spectrin and actin with low-ionic-strength buffers but was solubilized in Triton/KCl solutions (FIG. 4(A), lanes 4, 5, 10, and 11. Extraction of IOVs at pH 11.0 or by 1M KCl/KI, conditions known to release protein 4.1 and ankyrin (36), caused only partial solubilization consistent with p55 as a peripheral membrane protein (FIG. 4(B)). Extraction of IOVs with 1M KCl resulted in partial proteolysis of p55 (FIG. 4(B), lane 7).

A quantitative immunoblot assay determined ≈80,000 copies of p55 monomer per erythrocyte (23). Based on its mobility in SDS/polyacrylamide gels, p55 may also exist as a dimer on the membrane (FIG. 4(A), lane 13, arrowhead). Stoichiometrically, higher molecular weight cross-reactive p55 (40,000 copies per cell), possibly a precursor or dimeric form, is a significant component of the erythrocyte membrane (37). There was no evidence of cytosolic p55 and the copy number remained constant from reticulocytes to mature erythrocytes (data not shown). Trypsin treatment of intact erythrocytes did not alter p55 mobility in SDS/polyacrylamide gels, and indirect immunofluorescence localized p55 to the cytoplasmic face of the erythrocyte membrane (data not shown).

During separation of p55 from dematin, a protein kinase coeluted with purified p55 (3). The absence of any consensus sequences for kinase catalytic domains or a putative nucleotide binding site in the amino acid sequence of p55 suggests that p55 is not a protein kinase. Immunoprecipitation of p55 from metabolically $^{32}P_i$-labeled erythrocytes and kinase assay of immune complexes failed to detect any protein kinase activity (data not shown) (25).

Palmitoylation of p55

Figure 5:
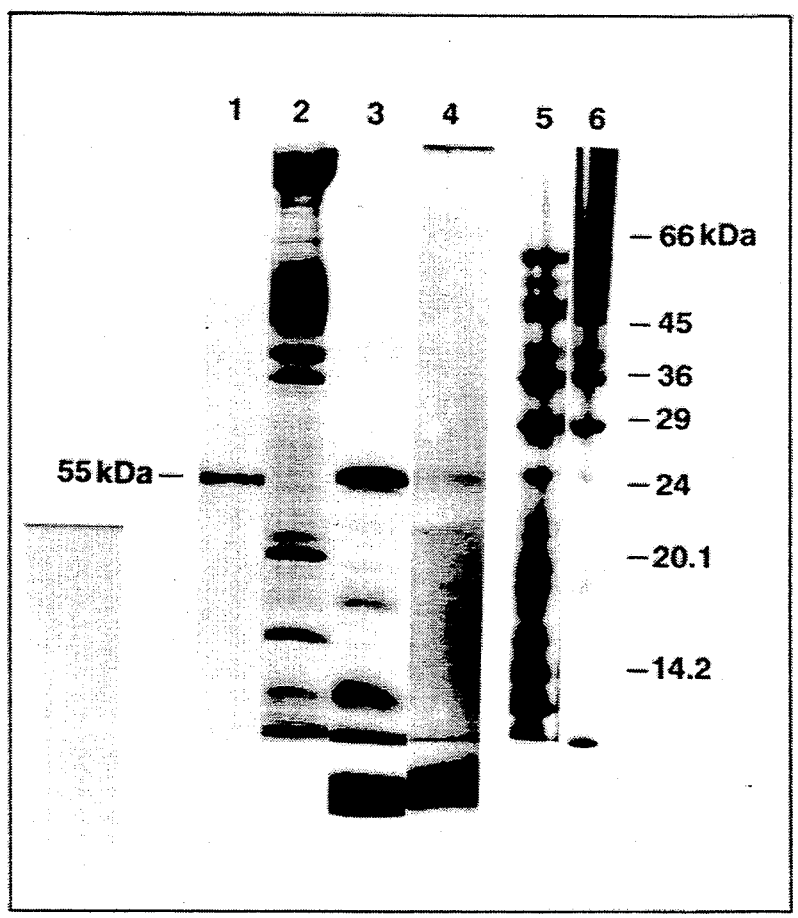
FIG. 5 is an SDS/PAGE analysis illustrating the palmitoylation of erythrocyte membrane proteins. Fresh erythrocytes were metabolically labeled overnight with [$^3$H] palmitate at 37° C. as described (24) and ghosts were analyzed by SDS/PAGE. Lane 1: pure p55; lane 2: Coomassie-stained [$^3$H] palmitate-labeled ghosts; lane 3: fluorograph of lane 2; lane 4: fluorograph of immunoprecipitated p55 from labeled ghosts (polyclonal antibodies to p55 were not as effective in immunoprecipitation experiments as in immunoblots; the lighter area under the immunoprecipitated p55 band is due to coprecipitated immunoglobulins); lane 5: silver-stained CNBr-cleaved peptides of purified p55; lane 6: fluorograph of CNBr-cleaved 55-kDa protein excised from lane 3.

Intact erythrocytes acylate several membrane proteins in vitro (24, 38, 39). More than 75% of exogenous [$^3$H]palmitate is incorporated into a protein of 55 kDa (24) (FIG. 5, lane 3). To establish whether the palmitoylated 55-kDa protein was p55, the following evidence was obtained: (i) in SDS/PAGE analysis of metabolically labeled erythrocyte plasma membranes, the most abundant [$^3$H] palmitoylated protein migrated with mobility identical to that of p55 (FIG. 5, lane 3); (ii) immunoprecipitation of solubilized membranes with polyclonal antibodies against p55 precipitated a $^3$H-labeled protein with mobility identical to that of p55 (lane 4); (iii) all the radiolabeled, CNBr-cleaved peptides of $^3$H-labeled 55-kDa protein (lane 6) were contained within the silver-stained CNBr-generated map of purified p55 (lane 5); and (iv) the extraction behavior of p55 from erythrocyte membranes (FIG. 4) and the specificity and kinetics of its palmitoylation were identical to those of [$^3$H] palmitoylated 55-kDa protein previously reported (24). These results suggest that p55 is the major palmitoylated protein of the human erythrocyte membrane.

Discussion

The reported experiments were originally initiated to examine the role of p55 in the inhibition of dematin's actin-bundling activity (2,3). The deduced primary structure of p55 and immune-complex kinase assays demonstrated that p55 does not contain any active kinase activity. The inhibition of actin-bundling activity of dematin therefore appears to be mediated by a protein other than p55 (3). However, these studies do not preclude an accessory role for p55 in the regulation of dematin's actin-bundling activity. Although the elution behavior of p55 is different from that of dematin on ion-exchange columns, a direct association between them cannot be excluded at this stage.

Northern analysis revealed p55 mRNA in uninduced K562 cells, a multipotent hemopoietic cell line. Upon induction of K562 cells with ara-C, a 2-fold increase in p55 message was observed (FIG. 2). The constitutive expression of p55 mRNA is in contrast to protein 4.1, ankyrin, band 3, and dematin, which are expressed late during erythropoiesis prior to their stable assembly into the membrane skeleton (29, 40).

Based on hydropathy and secondary structure analysis, p55 appears to be a peripheral membrane protein. This is supported by the observation that a significant amount of p55 can be eluted from IOVs by high-salt extractions in the absence of detergent (FIG. 4(B)). However, the remaining p55 is tightly associated with the membrane and its solubility behavior in Triton X-100 is reminiscent of an integral membrane protein (FIG. 4(A)). A similar solubility behavior has been observed with protein 4.2, another peripheral membrane protein (41). The detergent solubilization of p55 may be partly explained by the observation that it is the most abundantly palmitoylated protein (FIG. 5). Due to rapid turnover of bound lipid, salt-eluted p55 may contain significantly less palmitate. The existence of palmitoylated 55 to 57 kDa proteins of human erythrocyte membrane with similar lipid incorporation properties has also been previously noted (24, 39, 67). There are four cysteine residues in p55, including one in the SH3 motif, which may provide potential sites for palmitoylation (42) (SEQ ID NOS. 1 and 2). Since a consensus sequence of palmitoylated cysteine is not known, identification of palmitoylated residue(s) awaits separation and microsequencing of $^3$H-labeled peptides of p55.

Mutation analyses and direct enzyme inhibition assays indicate that the functional role of the SH3 motif in non-receptor tyrosine kinases is to downregulate their kinase activity (14, 15, 17). One can predict that the ligand(s) which binds to the SH3 motif may modulate the tyrosine kinase activity of oncoproteins and by definition may have anti-oncogene activities (15). In fact, the mechanism by which p47$^{gag\text{-}crk}$, which contains only SH2 and SH3 sequences, transforms cells may be partly due to the depletion of such a ligand via SH3 sequences (32). Moreover, the occurrence of the SH3 motif in cytoskeletal proteins suggests that this sequence may mediate interaction with ligand(s) common to signal-transducing molecules (6).

To identify ligands that interact with the SH3 sequence, it will be imperative to have a system where the interactions of various constituents can be reconstituted and quantified. The discovery of an actin-binding protein with an SH3 motif in yeast provides one such system (7). The human erythrocyte membrane provides another experimental system that has been well characterized (37). Moreover, the erythrocyte membrane contains another protein with an SH3 motif, α-spectrin (33-35). Purified α-spectrin or its SH3 motif may serve as a reagent to confirm the specificity of ligands for the p55 SH3 motif. Since analogs of erythrocyte membrane proteins exist in other cells, the identification of these ligands may have consequences beyond red-cell biology.

B. SPECIFIC EXAMPLES—GROUP II

Materials and Methods

Reagents

Enzymes used in guanylate kinase assay were purchased from Boehringer Mannheim and GMP was obtained from Sigma Chemical Company.

HPLC Assay of Guanylate Kinase Activity

The assay conditions for the measurement of guanylate kinase activity were similar to those described previously (46). The reaction mixture contained 1 mM [γ$^{32}$P]ATP (600 Ci/mmole), 0.5 mM GMP, 10 mM Tris-acetate, pH 7.0, 10 mM magnesium acetate, 50 mM KCl. After the addition of purified p55, the reaction was carried out for 10 min at 30° C. The $^{32}$P-labeled reaction products were analyzed by HPLC on a Patisphere SAX column. (Whatman). The elution conditions were adapted from a method by Whitman et al. (47). The samples were spiked with cold GDP and ATP and were loaded in H$_2$O. The column was washed for 10 min with H$_2$O, then eluted with 1.0M (NH$_4$)$_2$HPO$_4$, pH 3.8 (solvent B) at 1.0 ml min$^{-1}$. A linear gradient of 0 to 6% solvent B over 35 min was followed by a linear gradient of 6 to 18% solvent B over 30 min. The eluent passed through an in-line UV detector set at 254 nm followed by an in-line radioactivity detector (Radiomatic A140, Meriden, Conn.).

Spectrophotometric Assay of Guanylate Kinase

The coupled enzyme assay for guanylate kinase activity was carried out essentially as described previously (48). Briefly, the reaction mixture in 1.0 ml assay volume contained: 50 mM Tris-HCl (pH 8.0), 250 mM KCl, 10 mM MgCl$_2$, 1.5 mM phosphoenolpyruvate, 2 mM ATP, 0.25 mM NADH, 2.5 units pyruvate kinase and 3.3 units of lactate dehydrogenase. An appropriate concentration of purified p55 was added to the assay mixture and absorbance was stabilized for 2 min. The guanylate kinase reaction was started by the addition of GMP to a final concentration of 1.0 mM. The decrease in absorbance was measured for 4-5 min at 340 nm at 30° C.

Northern and Southern Blot Analyses

A human multiple tissue Northern blot containing 2 μg of polyA+ RNA in each lane was obtained from Clontech (Palo Alto, Calif.). The integrity and purity of RNA, obtained from apparently healthy human accident victims was ensured by the manufacturer. Northern blots were prehybridized for 4.0 hr in 5× SSPE (1× SSPE contained 180 mM NaCl, 10 mM sodium phosphate, pH 7.7, 1.0 mM EDTA), 50% formamide, 10×Denhardt's solution (1.0× Denhardt's solution contained 0.02% Ficol, 0.02% polvinylpyrolidone and 0.02% bovine serum albumin), 2% SDS and 100 μg/ml boiled sonicated salmon sperm DNA. A 1.1 kb cDNA fragment of p55 (43) as radiolabeled with [$^{32}$P]dCTP using a random primer kit (Amersham). Labelled cDNA was separated from unincorporated radioactivity by a gene clean kit (Bio 101 Inc., LaJolla, Calif.), denatured by boiling and added to a final concentration of 10$^6$ cpm/mm in the prehybridization buffer. Hybridizations were carried out for 18-24 hr at 42° C. After hybridization, membranes were washed at 65° C. in 0.2× SSC (1×SSC contains 150 mM NaCl, 15 mM sodium citrate, pH 7.0), 0.1% SDS and autoradiographed for 1-4 days.

Chromosome Mapping

The chromosomal localization of the p55 gene was performed using a human-hamster somatic cell hybrid panel as described previously (49).

Results p55 SH3 Motif and Guanylate Kinase Domain and Sequence Correction

Figure 6A:
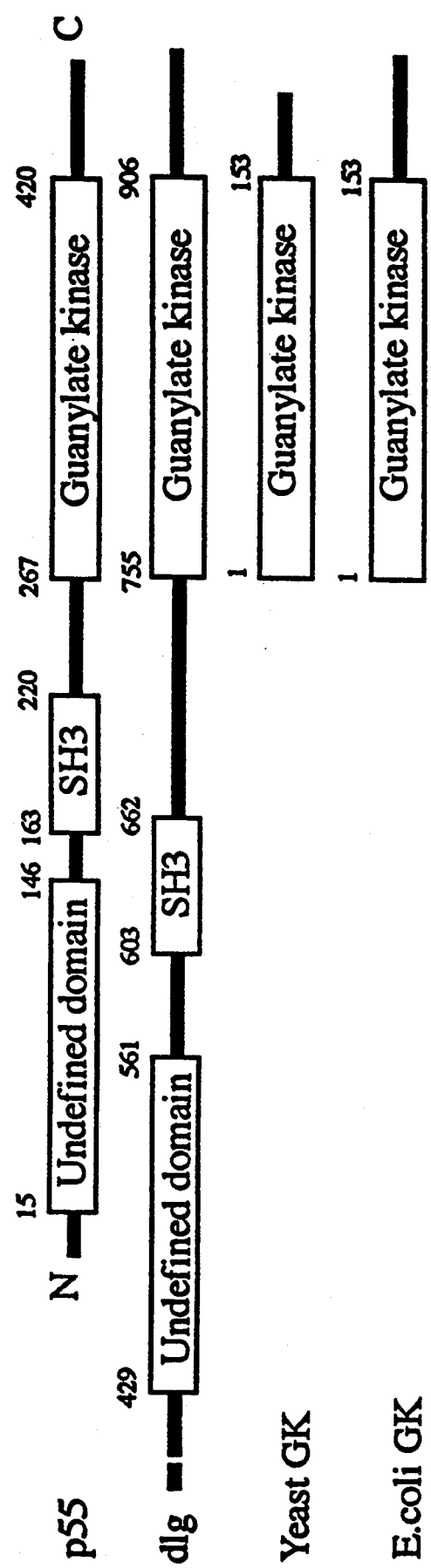
FIG. 6(A) is a schematic representation of the guanylate kinase domains in human erythroid p55, Drosophila dlg gene product, yeast and E. coil guanylate kinases. The sequence similarity with yeast guanylate kinase is shown only up to residue 153, although similarity of somewhat lesser extent extends for a further 30 amino acids of the yeast sequence. The line diagram outlines three putative domains in erythroid p55 (43): an N-terminal undefined domain, an SH3 motif and a C-terminal guanylate kinase domain.

The general organization of p55 protein and its relationship to the product of Drosophila tumor suppressor gene dlg and guanylate kinases is shown in FIG. 6(A). The primary sequence of erythroid p55 consists of 466 amino acids and includes an SH3 motif located between residues 164 and 223 (FIG. 6(A)). The SH3 motif of erythroid p55 is most similar (41.1% identity) to the SH3 motif found in the dlg gene product (50, 51). Both p55 and dlg contain an N-terminus sequence upstream of the SH3 motif which shares 25% sequence identity (FIG. (7A)). The function of the N-terminal domain defined by residues 15 and 146 is not yet known. Drosophila dlg gene product contains an additional N-terminal sequence of 428 amino acids which is not present in human erythroid p55 (45) (FIG. 6(A)).

The C-terminal half of erythroid p55, as defined by residues 267 and 420, shows 35.7% identity with the C-terminal domain of dlg gene product (FIG. 6(A)). Both erythroid p55 and Drosophila dlg gene product show significant sequence homology with the primary structures of yeast and E. coil guanylate kinases as illustrated by sequence alignments using the LALLIGN program from the FASTA software package (63). The guanylate kinase domain of p55 shares 35.3% sequence identity with yeast guanylate kinase and 30.9% sequence identity with E. coil guanylate kinase. Although sequence similarity between yeast guanylate kinase and p55 is shown only up to residue 420 (FIG. 6(A)), relatively less significant sequence similarity extends further downstream of residue 420 and includes essentially all remaining C-terminal residues of erythroid p55. In summary, the entire amino acid sequence of known guanylate kinases is contained within the C-terminal half of erythroid p55.

Dot matrix alignment of guanylate kinase domains in erythroid p55, Drosophila dlg gene product, yeast and E. coli guanylate kinases indicated lack of any repeated amino acid sequences within the guanylate kinase domains (FIG. 6(B)). It may be noted that the primary structure of erythroid p55 also contains a noticeable cluster of seven lysine residues located between SH3 motif and guanylate kinase domain (amino acids 223–267). The significance of this cluster of positively charged residues preceding the guanylate kinase domain of p55 is at present not known.

During the course of sequence alignments using the guanylate kinase domain of erythroid p55, we identified a new member of the guanylate kinase family in vaccinia virus protein A57R (30% sequence identity; 63% similarity: see reference 52, accession number P21074). The aligned sequences represent residues 325 to 403 of p55 and residues 2 to 80 of protein A57R. Although the function of protein A57R is not known, sequence alignment suggests that it may represent the first viral member of guanylate kinases.

Guanylate kinase catalyzes phosphorylation of GMP to GDP in presence of magnesium ATP in the following reversible reaction: GMP+ATP=GDP+ADP. Yeast guanylate kinase as well as erythroid p55 contain a signature sequence in their primary structures, GXXGXG, which provides a nucleotide binding site during catalysis (43, 55). This signature sequence is usually followed by a basic amino acid such as lysine in yeast guanylate kinase. The earlier reported amino acid sequence of erythroid p55 contained a proline at this position (SEQ ID NO. 2, residue 295) instead of a basic amino acid. Since this region of the p55 guanylate kinase domain cDNA contains high G and C content and secondary structure, we resequenced the same cDNA templates with improved DNA sequencing techniques. Indeed, the original codon CCC encoding proline was found to be CGC, which encodes arginine. In addition, codon TTC was corrected to GTC, resulting in a change of phenylalanine to valine at position 314 (SEQ ID NO. 2) in the guanylate kinase domain of erythroid p55. Both yeast and E. coli guanylate kinases contain a valine residue at the equivalent positions, respectively (FIG. 6(B)). In summary, the guanylate kinase domain of erythroid p55 shares extensive sequence similarity with the primary structures of yeast and E. coli guanylate kinases.

Guanylate Kinase Activity of Purified p55

Figure 7A:
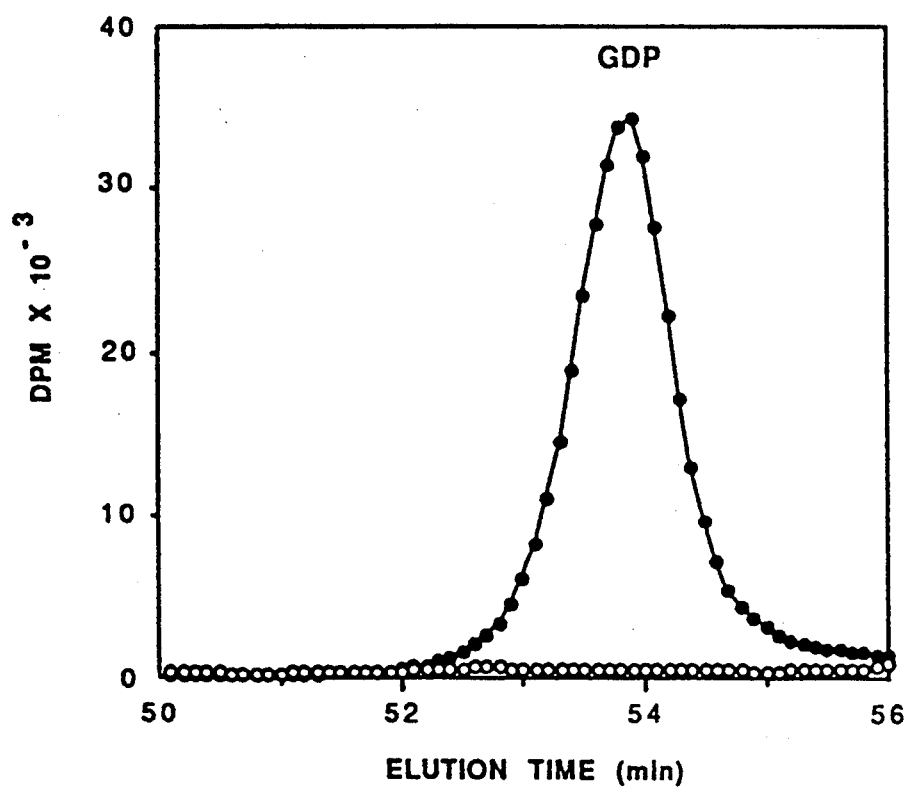
FIGS. 7(A) and (B) provide assay results of guanylate kinase activity of purified p55. Purified p55 was isolated from human erythrocyte membranes as described previously (3). Filled circle represents assay mixture containing p55 and open circle represents control tubes without p55. Simultaneous monitoring of unlabeled nucleotides and radioactivity was carried out on an HPLC anion exchange column. Position of nucleotides was determined by the addition of unlabeled standards in assay mixture. Guanylate kinase assay was standardized using purified enzyme isolated from E. coil (a gift from Dr. D. Gentry, NIH, Bethesda, Md.).
Figure 7B:
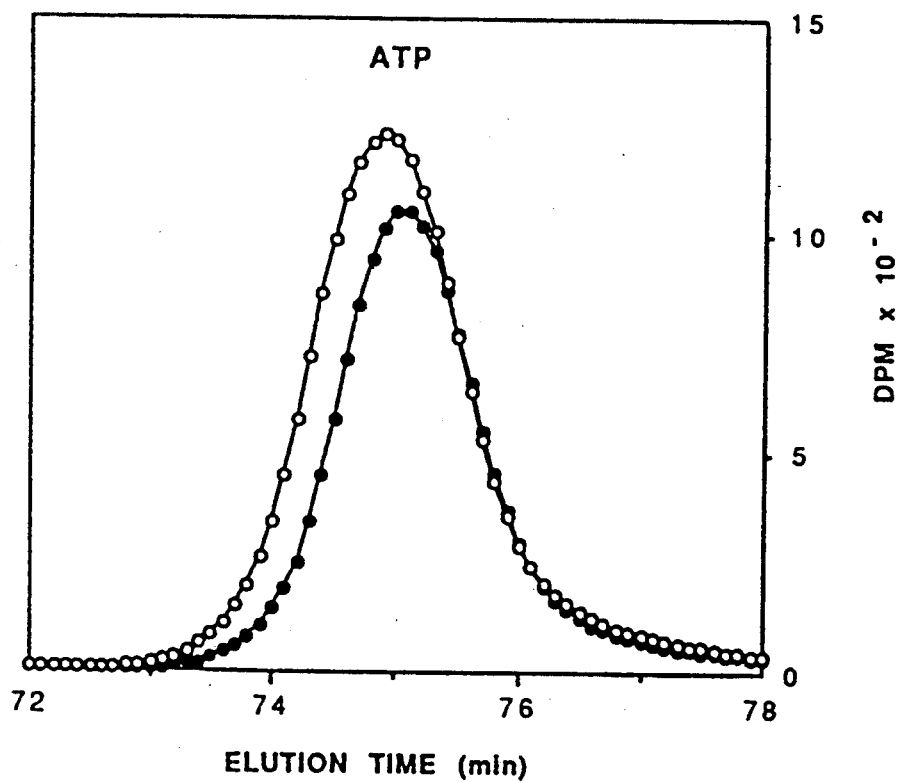
FIG. 7(B) results illustrate that concomitant utilization of [γ$^{32}$P]ATP was consistent with the production of GDP during the course of reaction.

In view of the extensive sequence similarities between the C-terminal domain of human erythroid p55 and guanylate kinases, we examined whether erythroid p55 is an enzymatically active guanylate kinase. Purified p55 was isolated from human erythroid membranes as described earlier (3). Briefly, ghosts were detergent-extracted in low ionic strength buffers and skeletal proteins were dissociated in detergent-free buffers. P55 was purified by sequential anion exchange chromatography using DEAE-Sephacel and Mono Q columns by fast protein liquid chromatography (3). Purified p55 was assayed for guanylate kinase activity in a reaction mixture that contained [$\gamma^{32}$P]ATP and unlabeled GMP (FIG. 7). Production of [$^{32}$P]GDP was monitored by an anion-exchange guanylate kinase assay using high pressure liquid chromatography as described in the Methods and Materials section. No detectable [$^{32}$P]GDP was produced in control experiments lacking erythroid p55 (FIG. 7(A)). The corresponding utilization of [$\gamma^{32}$P]ATP as shown in FIG. 7(B) is consistent with the amount of [$^{32}$P]GDP produced in the reaction. The positions of cold nucleotides were determined by UV absorption of column eluents. Alternatively, the guanylate kinase activity of purified p55 was quantified by a spectrophotometric assay as described in the preceding Methods and Materials section (48). Purified erythroid p55 converted 12–14 nmoles of GMP to GDP per min per mg protein.

Northern and Southern Blot Analyses

Figure 8A:
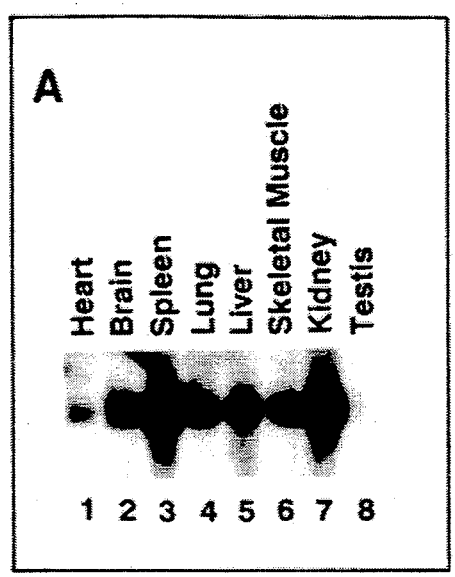
FIG. 8(A) is a mouse multiple tissue Northern blot obtained from CLONTECH Laboratories, Palo Alto, Calif. Each lane contain 2 μg of polyA+RNA. A 1.1 kb EcoRI-digested cDNA probe of human erythroid p55 was radiolabeled using a random primer kit (Amersham). Transcripts of 2.0 kb were detected in tissues examined.
Figure 8B:
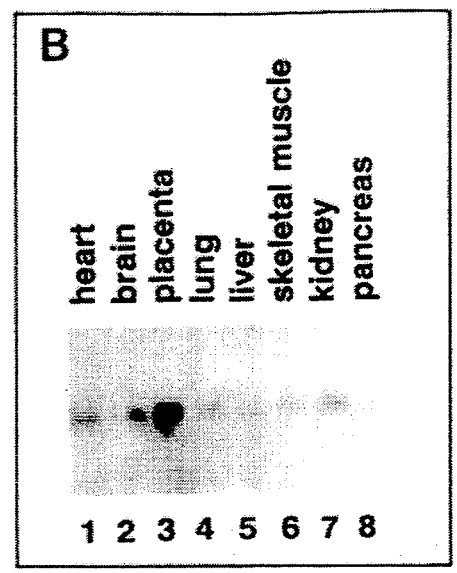
FIG. 8(B) is a human multiple tissue Northern blot. The experimental conditions were the same as above except the stringency of washings was increased by using 0.1×SSC and 0.1% SDS at 65° C. Again 2.0 kb transcripts of p55 were detected in all tissues examined.

It is now well established that isoforms of erythroid membrane proteins including spectrin, protein 4.1, ankyrin and band 3 are present in diverse group of cells and tissues (53). Hence we examined the expression of p55 mRNA in a variety of non-erythroid tissues. A 1.1 kb cDNA fragment of human erythroid p55 was used to probe Northern and Southern blots (FIGS. 9(A) and (B) and FIG. 9. The cDNA probe was originally excised with EcoRI and spans almost entire coding region of the p55 cDNA sequence (43). The probe hybridized with 2.0 kb transcripts in both mouse and human tissues (FIGS. 9(A) and (B)). P55 transcripts were detected in heart, brain, spleen, lung, liver, skeletal muscle, kidney, pancreas, placenta, and marginally in testis (FIG. 8(A), lane 8). It should be noted that the human Northern blot (FIG. 8(B)) was processed under stringent conditions at 65° C., which is likely to have caused diminution in hybridization signals. Perhaps for this reason, we did not detect the 4.0 kb mRNA which has previously been demonstrated in erythroid precursor cells (43). Erythroid p55 transcripts were also detected in human platelets and monocytes (data not shown). At this stage it is not known whether corresponding amounts of p55 protein are synthesized in these non-erythroid tissues. The development of monoclonal antibodies against erythroid p55, as described in the next set of Specific Examples, will permit detection and quantitation of p55-related antigens in these tissues.

Figure 9:
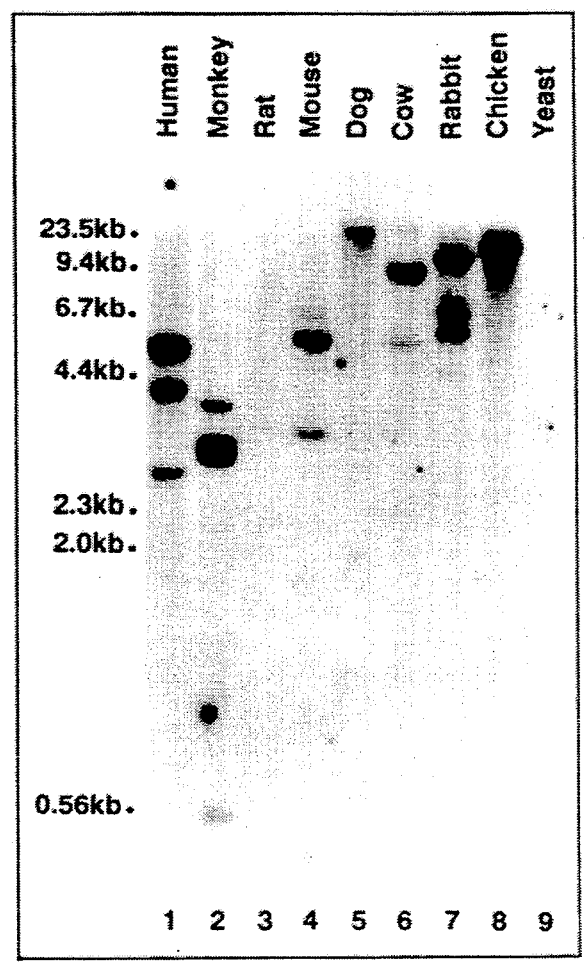
FIG. 9 is a Southern blot analysis of genomic DNA from nine eukaryotic species. Blot contains 8.0 μg of genomic DNA per lane. DNA was digested with EcoRI and separated on a 0.7% agarose gel as described in CLONTECH instructions. All other conditions were same as described in FIG. 8. Rat genomic DNA (lane 3) shows very faint hybridizing signals and no signal was detected in yeast (lane 9). It should be noted that the hybridization pattern in human DNA (lane 1) shows two closely spaced bands of approximately 6.0 kb in the original autoradiogram.

The conserved distribution of erythroid p55 transcripts in mouse and human tissues suggested that the erythroid p55 gene may be similarly conserved. In fact, hybridizing bands of homologous genes were detected by Southern blotting with a 1.1 kb cDNA probe (described above) in almost all animal species as shown in FIG. 9. Rat genomic DNA produced a weak hybridization signal (lane 3) and no signal was detected in yeast genome under these hybridization conditions (FIG. 9, lane 9). The detection of multiple hybridizing bands in EcoRI-digested human genomic DNA (lane 1) is consistent with two internal EcoRI sites present in p55 cDNA (43). It is interesting to note that the p55 cDNA probe which essentially spans the entire coding sequence detected a single hybridizing band of 20 kb in chicken DNA (lane 8). Moreover, the size of this band is consistent with the calculated size (20 kb) of Drosophila tumor suppressor gene dlg (45).

To examine the proximity of the p55 gene to known genetic markers including tumor suppressor genes and oncogenes (54), we decided to map the p55 locus on human chromosomes. Again, a 1.1 kb cDNA probe of erythroid p55 was used to detect hybridizing bands in Southern blots containing DNAs from human/hamster somatic cell hybrids. The hybridization signals segregated only with Xq24-qter as summarized in TABLE 1, strongly suggesting that the erythroid p55 gene is located within this region of the human X chromosome.

TABLE 1

HYBRIDIZATION PATTERN OF HUMAN ERYTHROID P55 WITH DNAs FROM HUMAN-HAMSTER SOMATIC CELL HYBRIDS

| Chromosome[a] | Segregation Pattern[b] | | | | Discordant Fraction[c] |
|---|---|---|---|---|---|
| | +/+ | −/− | +/− | −/+ | |
| 1 | 3 | 0 | 6 | 0 | 0.67 |
| 2 | 2 | 0 | 5 | 0 | 0.71 |
| 3 | 4 | 0 | 5 | 0 | 0.56 |
| 4 | 3 | 0 | 6 | 0 | 0.67 |
| 5 | 4 | 0 | 5 | 0 | 0.56 |
| 6 | 4 | 0 | 4 | 0 | 0.50 |
| 7 | 4 | 0 | 5 | 0 | 0.56 |
| 8 | 4 | 0 | 5 | 0 | 0.56 |
| 9 | 2 | 0 | 7 | 0 | 0.78 |
| 10 | 4 | 0 | 4 | 0 | 0.50 |
| 11 | 4 | 0 | 5 | 0 | 0.56 |
| 12 | 4 | 0 | 4 | 0 | 0.50 |
| 13 | 4 | 0 | 5 | 0 | 0.56 |
| 14 | 5 | 0 | 3 | 0 | 0.38 |
| 15 | 2 | 0 | 7 | 0 | 0.78 |
| 16 | 6 | 0 | 3 | 0 | 0.33 |
| 17 | 3 | 0 | 6 | 0 | 0.67 |
| 18 | 4 | 0 | 5 | 0 | 0.56 |
| 19 and 19pter-q13[d] | 8 | 0 | 1 | 0 | 0.11 |
| 20 | 8 | 0 | 1 | 0 | 0.11 |
| 21 | 5 | 0 | 4 | 0 | 0.44 |
| 22 | 4 | 0 | 5 | 0 | 0.56 |
| X and Xq24-qter[e] | 9 | 0 | 0 | 0 | 0.00 |
| Y | 0 | 1 | 8 | 0 | 0.89 |

[a] Human chromosome complements of the hybrids were determined by isozyme and cytogenetic techniques (64). In addition, hybrid DNAs were analyzed with cloned DNA probes assigned to each of the human autosomes and the X chromosome.
[b] Column designations: +/+ hybridization signal and chromosome both present; −/− hybridization signal and chromosome absent; +/− hybridization present but chromosome absent; and −/+ hybridization absent with chromosome present.
[c] Calculations of the discordant fractions, hybrids with a rearranged chromosome or in which the chromosome was present in less that 15% of cells were excluded.
[d] For 8 hybrids derived from a fusion of Chinese hamster E36 cells with leukocytes from a female carrier of the balanced translocation L(X:19)(q24::q13)(65), this category represents the 19pter-q13 derivative chromosome.
[e] This category includes one hybrid with an intact X chromosome as the sole human complement and 8 hybrids that had retained Xq24-qter.

Discussion

In the above experiments we demonstrated that the most abundantly palmitoylated protein of the human erythroid membrane, p55, contains an enzymatically active guanylate kinase domain (GMP kinase EC 2.7.4.8). This is the first demonstration of a membrane-associated, fatty acid-acylated protein that can catalyze production of GDP from GMP at the plasma membrane. The guanylate kinase domain of erythroid p55 is located in its C-terminal half and shows significant sequence similarity with the entire amino acid sequence of both yeast and E. coil guanylate kinases (55). The primary structure of mammalian guanylate kinases is not known and one would expect even more significant sequence similarities between p55 and mammalian guanylate kinases to be forthcoming. The calculated specific guanylate kinase activity of purified p55 was significantly lower than the known specific activity value for yeast guanylate kinase (55). At this stage the reasons for this difference are not clear, but several factors such as detergent extraction during purification and storage conditions may influence enzyme activity in vitro. In addition, erythroid p55 is known to be extensively phosphorylated in vivo (3). The phosphorylation and palmitoylation state of purified p55 is not yet known and their effects on guanylate kinase activity remain to be determined. It is also possible that the SH3 motif which precedes the guanylate kinase domain may modulate the enzymatic activity of erythroid p55 in vivo. Finally, membrane proteins may be identified which interact with p55 and modulate its guanylate kinase activity.

The observed sequence conservation between human erythroid p55 and Drosophila tumor suppressor dlg gene product suggests the possibility of a similar functional role for p55 in non-erythroid tissues. Woods and Bryant (45) predicted that dig gene product may exert its tumor suppressive effects by modulating levels of GDP and GTP at the plasma membrane. The levels of guanine nucleotides may in turn influence steps in ras proto-oncogene pathway (56). Indeed, ras G proteins are functionally inactive when bound to GDP and, like erythroid p55, are also known to be palmitoylated suggesting their similar location on the plasma membrane (57). In this context, we note that the mechanism of action of known tumor suppressor genes such as p53 and NF1 involves modulation of guanine nucleotide levels at the plasma membrane (54, 58). Since isoforms of high molecular weight G proteins and ras have been documented in the human erythroid membrane (59), the p55 associated with erythroid membrane provides potentially an excellent model system to study biochemical pathways involving guanine nucleotides, SH3 motif and cytoskeletalmembrane interactions.

The results obtained by Northern and Southern blot analyses clearly establish that isoforms of erythroid p55, as other erythroid membrane proteins, show highly conserved tissue distribution. More interestingly, the gene of erythroid p55 was localized to a region on the long arm of the X chromosome (Xq24-qter) where loci for several genetic disorders have been mapped previously (60). After completion of this work, Metzenberg and Gitschier (61) reported isolation of a gene from the CpG island 30 kilobases 3' to the human factor VIII gene in Xq28. DNA sequencing of the corresponding transcript revealed that this gene is identical to human erythroid p55 (43). The gene was localized between Factor VIII and G6PD genes and its sequence conservation is consistent with the results reported here (61). There are eighteen Xq28-linked diseases where the corresponding genes have not yet been identified. These include: Emery-Dreifuss muscular dystrophy, centronuclear myopathy, endocardial fibroelastosis, myopathy with excessive autophagy, Dyskeratosis congenita, incontinentia pigmenti, chondrodysplasia punctata, mental retardation with skeletal dysplasia, mental retardation with anophthalmos, adrenoleukodystrophy, Bornholm eye disease, Goeminne syndrome, hydrocephalus, MASA syndrome, Waisman syndrome, spastic paraplegia, manic depressive psychosis and MRX3 mental retardation.

The chromosomal localization of the erythroid p55 gene makes p55 a candidate for any of these diseases. Moreover, the membrane location of erythroid p55 suggests focusing in particular on diseases which involve defects in cell membranes and cell-cell contacts such as those seen in neuromuscular disorders. Finally, the tumor-suppressive effects of Drosophila dlg gene product suggest investigating a potential linkage between Dyskeratosis congenita and the p55 gene. Dyskeratosis congenita is a recessive disorder which causes dermatological abnormalities, bone marrow hypofunction and a predisposition to neoplasia in early adult life (62). Now that characterization of erythroid p55 has begun and necessary reagents are being developed, it is feasible to subject such enquiries to experimental test. Assays employing p55 for hemolytic anemia and Dyskeratosis congenita have already been implemented as described in the following set of Specific Examples.

C. SPECIFIC EXAMPLES—GROUP III

Clinical Applications

Nucleic acid and protein-based methods for screening and diagnosing abnormalities in p55 are contemplated as within the scope of the present invention. For example, knowing the sequence of p55, DNA or RNA probes can be constructed and used to diagnose mutations through hybridization with genomic DNA or transcripts in cells or tissue using a variety of techniques. Oligonucleotide probes can be similarly used to detect quantitative changes in expression. A mixture of different probes, i.e. "probe cocktails," can also be employed to test for multiple mutations. With respect to nucleic acid-based testing, genomic DNA may be used directly or may be amplified enzymatically in vitro by using PCR prior to analysis. DNA sequence detection may be accomplished, for example, using probes as described above, or through direct DNA sequencing, the use of restriction maps, differences in electrophoretic mobility or any of a number of other methods known to those skilled in the art.

With respect to protein-based testing, antibodies can be generated to p55 using standard immunological techniques, fusion proteins or synthetic peptides. Monoclonal antibodies can also be produced adapting now conventional techniques (68). It will also be appreciated that antibody fragments, i.e. Fab' fragments, can be similarly employed. Immunoassays, for example ELISAs, in which the test sample is contacted with antibody and binding to the gene product detected, can provide a quick and efficient method of determining the presence and quantity of p55.

With the characterization of p55 and its function, functional assays can also be used for diagnosis and screening and to monitor treatment. For example, enzymatic testing to determine levels of gene function, rather than direct screening of the p55 gene or product, can be employed. In the present invention, the ability of p55 to catalyze the conversion of GMP to GDP or any other function later determined, can be assayed and quantified.

Identification, cloning and sequencing of p55 also has therapeutic implications. In conventional replacement therapy, purified p55 or its functional equivalent is provided to the patient in therapeutically effective amounts. Sufficient amounts of p55 for treatment can be obtained, for example, through cultured cell systems or synthetic manufacture. Drug therapies which stimulate or replace can also be employed. Delivery vehicles and schemes can be specifically tailored to p55 or the particular drug being administered. Treatment can also take the form of modulation of the function of defective p55 or by modification of another protein or step in the pathway in which p55 participates in order to correct the physiological abnormality.

Modulation of p55 function can be accomplished by the use of therapeutic agents or drugs which can be designed to interact with different aspects of p55 protein structure or function. Efficacy of a drug or agent can be identified by a screening program in which p55 modulation is monitored in vitro in cell systems. Gene therapy using recombinant technology to deliver the gens or viral or other vectors which will supply the patient with gene product in vivo can also be employed.

Since p55 may function as a tumor suppressor, increasing the supply of p55 through supplementation or replacement or increasing in vivo production may have a beneficial effect in cancer treatment.

Immunoassays

ELISA

Microtiter plates (Immulon 2, Dynatech Laboratories) were incubated 1 hr with 50 microliters containing 100 nanograms of purified p55 as antigan. Plates were then rinsed with Tris-buffered saline (TBS) and incubated for 1 hr with blocking buffer containing TBS/0.1% Tween-20/0.02% $NAN_3$/5% human serum. Plates were rinsed with TBS prior to usage. All steps were performed at room temperature. To initiate the assay, 50 microliter aliquots of anti-p55 antibody (polyclonal or monoclonal), generally comprising a 1:100 dilution of polyclonal serum in blocking buffer, or undiluted hybridoma supernatant containing monoclonal antibodies, were pipetted into wells of the microtiter plate. Plates were incubated for 1 hr with primary antibody, following which antibody was removed by aspiration and plates rinsed with several applications of TBS/0.1% Tween-20/0.02% $NaN_3$. Aliquots of 100 microliters of alkaline-phosphatase conjugated goat-anti-rabbit (for polyclonal serum) or goat-anti-mouse (for monoclonal antibodies) antibodies, diluted 1:500 in blocking buffer were pipetted into the wells and incubated for 1 hr. Antibody conjugate was aspirated from wells and plates were rinsed with several changes of TBS/0.1% Tween-20/0.02% $NaN_3$. Aliquots of 150 microliters of chromogenic substrate for alkaline phosphatase, p-nitrophenyl phosphate, were pipetted into wells, and plates were incubated until the yellow reaction product was measurable by densitometry at 400 nm. Densitometry values above background indicated presence of p55 antibody in the sample assayed, and were approximately proportional to the quantity of anti-p55 antibody present.

The ELISA assay described above was used to screen for monoclonal anti-p55 antibodies in hybridoma supernatants and positive clones were obtained.

Variant Forms of Immunoassay

Quantitative immunoassays can also be employed using, for example, the following two approaches. For a competition assay, constant amounts of p55 antigen are applied and bind to the microtiter plate wells. After blocking as above, increasing amounts of solubilized p55 antigen are added to the wells. Plates are then incubated with a constant amount of anti-p55 antibody per well. A standard curve is thus obtained, in which the densitometric value is inversely proportional to the amount of p55 added in soluble form. The amount of p55 in unknown specimens may be quantitated by adding such specimens to assay wells in parallel with p55 standards used to generate the calibration curve.

A two-site sandwich assay can likewise be devised. Two anti-p55 antibodies are generated, with differing specificities for defined p55 epitopes. These antibodies may be most appropriately generated as monoclonal antibodies, but polyclonal antibodies generated against defined peptide fragments of p55 may be equally useful.

One antibody serves as capture antibody, with which microtiter plate wells are first coated. Coated plates are blocked in blocking buffer and then incubated with aliquots of p55 antigen. The second antibody is then applied as the marker. Such a marker antibody may be biotinylated, or may be directly conjugated with a marker enzyme such as alkaline phosphatase or horseradish peroxidase. If the marker antibody is biotinylated, then presence of antigen may be detected by subsequent addition of avidin conjugated to a marker enzyme. In the final step, chromogenic or other substrate for the marker enzyme is added to the microplate wells and enzyme product detected by densitometry, scintillometry, autoradiography, fluorometry, or other means. Quantitative values derived from this assay are linearly proportional to amount of soluble p55 antigen added.

Western Blot Analysis

A quantitative Western blot assay for p55 was developed using anti-p55 polyclonal antibody, being similarly applicable to monoclonal antibodies, as follows. Erythrocyte "ghosts" were prepared from fresh red blood cells by extraction with Triton X-100 following conventional ghost preparation procedures. Ghosts comprise non-detergent extractable proteins of the erythrocyte cytoskeleton, including p55 as well as previously identified proteins such as spectrin, ankyrin, band 4.1, and band 4.9. The concentration of protein in samples of erythrocyte ghosts was determined by Lowry or BCA (bicinchoninic acid) assay procedures. Ghost proteins were completely solubilized in 5× SDS sample buffer (standard buffer for preparation of samples for SDS gel electrophoresis) and were separated by electrophoresis on a 10% acrylamide SDS gel. A series of samples of pure p55 in known, increasing amounts was electrophoresed in parallel with the unknown samples.

Following electrophoresis, proteins resolved in the gel were transferred to a nitrocellulose membrane by known procedures (66). The membrane was incubated with 25% isopropanol/10% acetic acid for 15 min to fix transferred proteins irreversibly to its surface and prevent their elution during subsequent steps. The membrane was then washed with distilled water, and rinsed for 30 min in phosphate-buffered saline (PBS)/0.1% Tween-20. To initiate the assay, the membrane was incubated for 1 hr at room temperature with a 1:500 dilution of polyclonal anti-p55 antibody in PBS/Tween-20 containing 3% bovine serum albumin. Unbound antibody was then removed with three washes in PBS/Tween for 10 min each. Bound antibody was detected by incubating the membrane for 1 hr with a 1:4000 dilution of $^{125}$I-Protein A in PBS/Tween/3% BSA, after which excess Protein A was removed by multiple washes with PBS/Tween.

Finally, areas of the membrane corresponding to the position of protein bands visualized by staining either the gel or the membrane with non-specific protein stains (e.g., Coomassie Blue for the gel or Ponceau S for the membrane) were cut out and transferred to scintillation vials. Radioisotope amounts in each protein band were measured in a Beckman gamma counter (model 5500B).

Figure 10A:
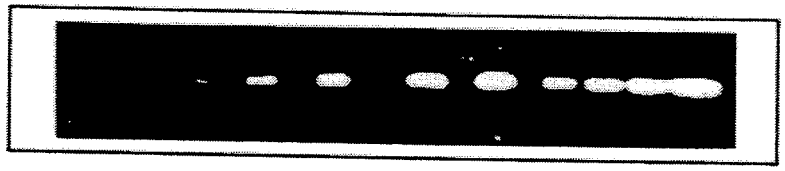
FIG. 10 provides a Western blot assay and graph which illustrate the linear relationship between amount of $^{125}I$ measured and the amount of p55 in the electrophoresed sample.
Figure 10B:
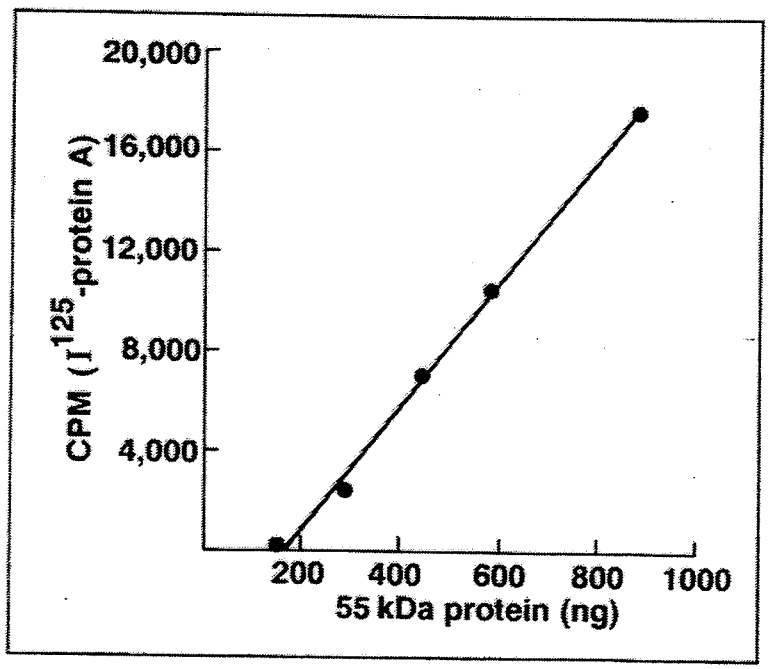

FIG. 10 indicates the linear relationship between amount of $^{125}$I measured and amount of p55 protein in the electrophoresed sample. Above the calibration curve, the autoradiogram of the membrane indicates pictorially the same linear relationship—from left to right are increasing amounts of p55 in contiguous gel lanes, comprising the standard curve; the rightmost 4 bands represent unknown samples.

Immunofluorescence/Immunohistochemistry

The p55 antigen can be detected in cells or tissues by immunofuorescence or immunohistochemistry. As an example, human erythrocytes in conventionally prepared blood smears were fixed on microscope slides with cold ($-70°$ C.) acetone for 5 min. Slides were rinsed thoroughly with distilled water and incubated for 15–20 min in blocking solution containing PBS/5% serum. Slides were then incubated in a 1:200 dilution of anti-p55 antibody in blocking solution for 1 hr at room temperature. Following incubation, slides were rinsed 3 times for 10 min each in PBS solution. Slides were then incubated in a 1:200 dilution of fluorescein isothiocyanate (FITC)-conjugated goat anti-rabbit IgG, followed by 3 washes of 10 min each in PBS to remove unbound fluorescent antibody conjugate. Slides were mounted in 90% glycerol in PBS with 0.1% p-phenylenediamine and observed in a Zeiss microscope equipped with phase contrast and fluorescence optics.

In normal mature erythrocytes, p55 appeared to be uniformly distributed in the membrane skeleton. In contrast, in erythrocytes infected with P. falciparum malaria parasites, p55 appeared to be preferentially distributed at the cell periphery, and was reduced in total amount per cell.

Figure 11:
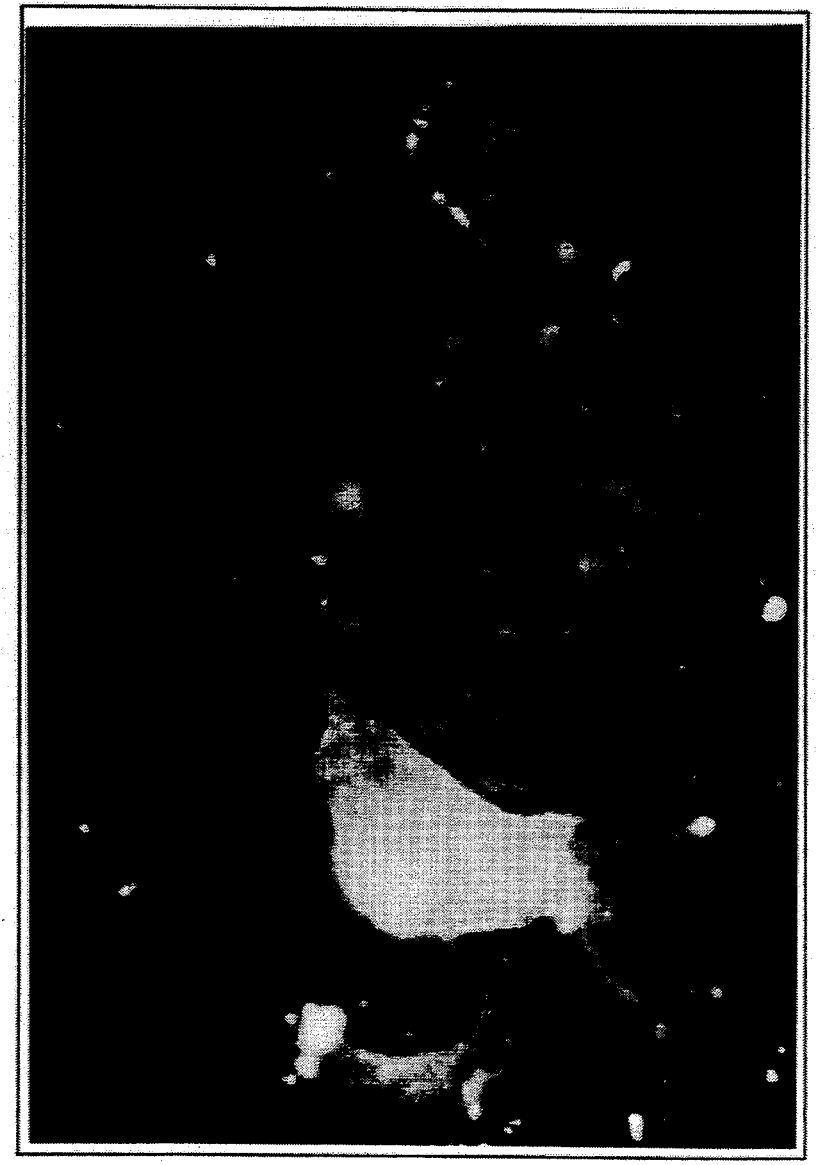
FIG. 11 illustrates the localization of p55 to the surface of cultured human breast carcinoma cells by immunofluorescence.

The distribution of p55 in human (and non-human) tissues other than erythrocytes can likewise be determined by immunofluorescence or immunohistochemistry. Immunohistochemistry involves substitution of a nonfluorescent but colored enzymatic product for the fluorescent label (FITC above). In clinical assays for a variety of disease states, including many forms of cancer, immunohistochemistry is routinely used as a principle laboratory diagnostic technique. The relationship of p55 to the signal transduction/oncogene pathway, together with its homology to the Drosophila tumor suppressor factor suggest that p55 may be a useful marker for tumorigenic events (e.g., tissue proliferation and metastasis) in cells and tissues other than erythrocytes. Such an experiment has been carried out which localized p55 to the surface of cultured human breast carcinoma cells by immunofluorescence (FIG. 11).

Diagnostic Marker

Hereditary Hemolytic Anemias

Figure 12A:
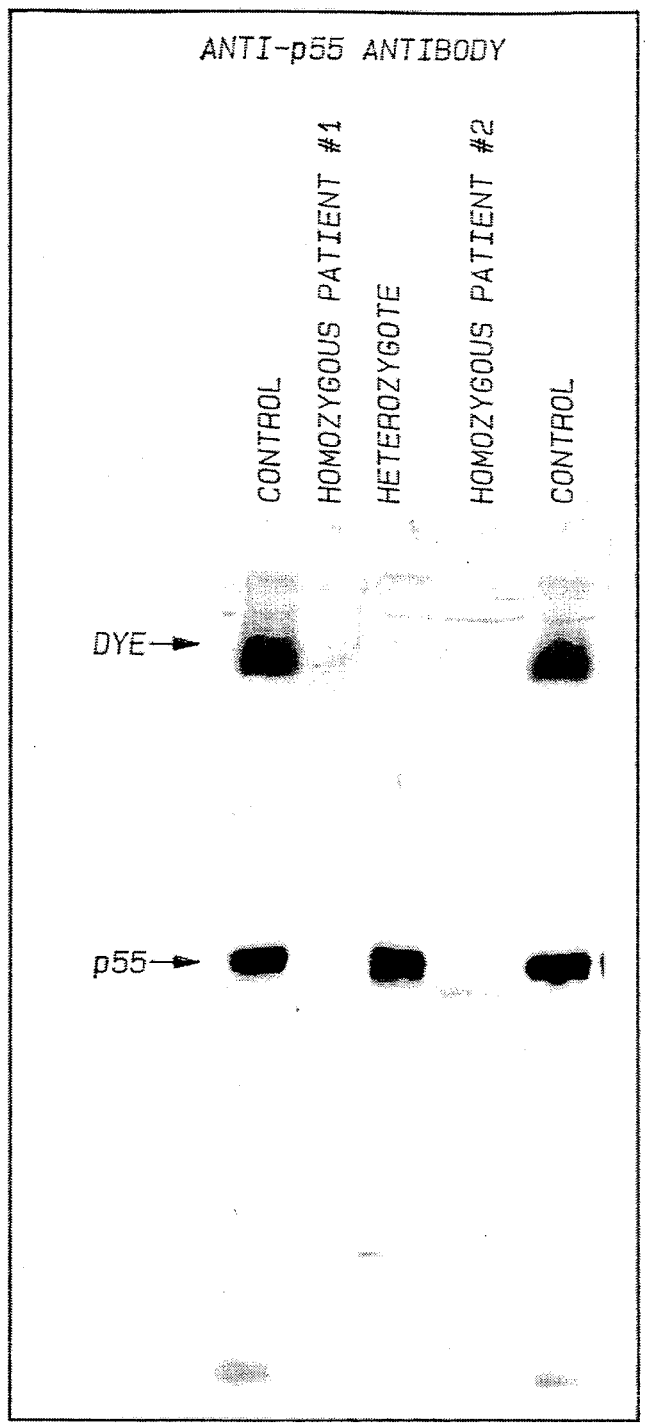
FIG. 12(A) shows the results of an assay using anti-p55 antibody.
Figure 12B:
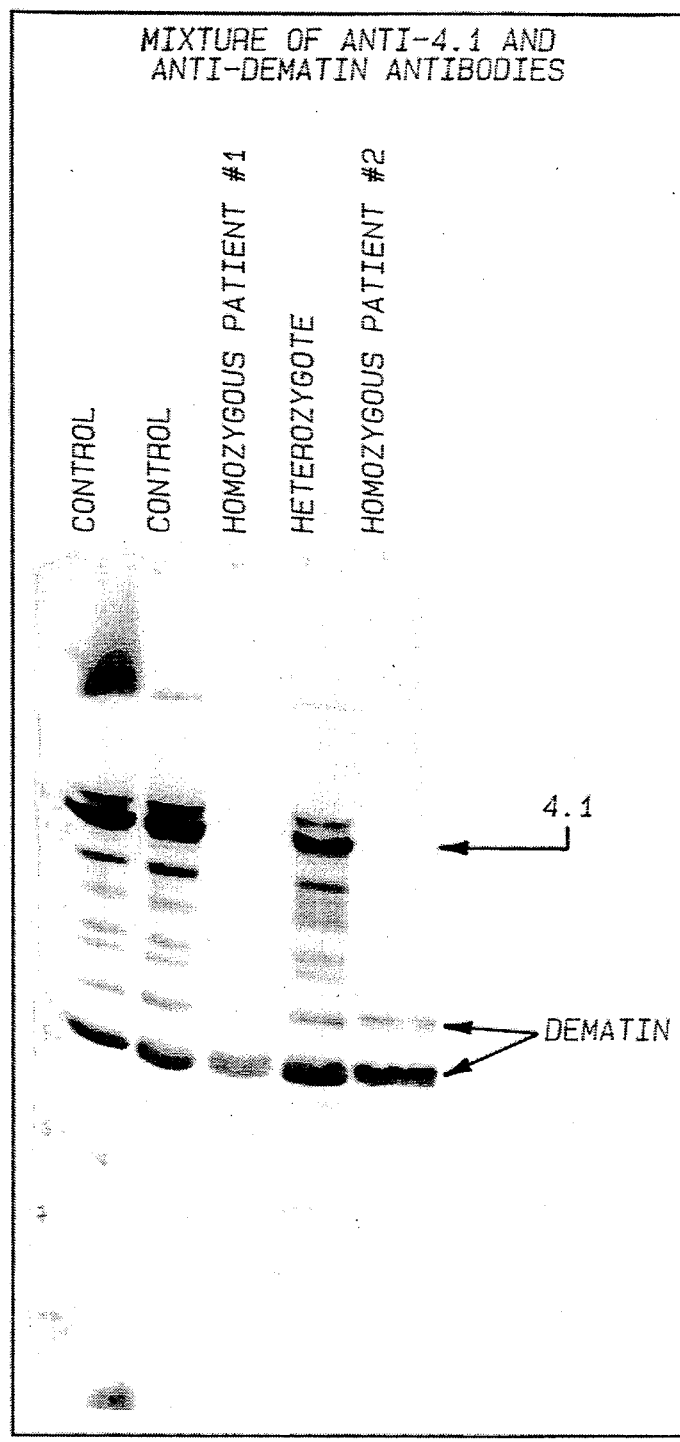
FIG. 12(B) shows the results of an assay using a mixture of anti-4.1 and anti-dematin antibodies.

Elliptocytosis is a heterogeneous human hemolytic anemia. In one form of this disorder, a hereditary deficiency in the erythrocyte membrane protein band 4.1 (FIG. 12(B)) has been suspected as the primary cause of disease. The above described Western blot assay has been used to examine p55 antigan in erythrocyte samples from elliptocytosis patients (homozygotes). Results show the nearly total absence of the p55 band in these patients, in comparison with normal healthy specimens (control) and heterozygotes (FIG. 12(A)). It is not clear whether absence of p55 is the primary defect or a secondary one; however, the p55 Western blot assay provides a means to diagnose this hereditary disease.

Dyskeratosis Congenita.

Figure 13A:
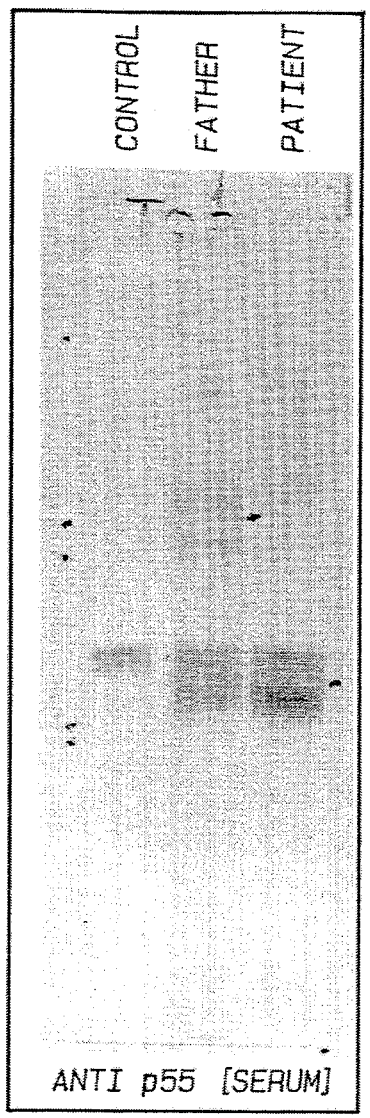
FIGS. 13(A) and (B) are a Western blot analysis (different stages of blot development) of Dyskeratosis congenita patient samples which depicts higher MW and apparently degraded forms of p55 in the patients tested. Controls (not shown) using anti-4.1 and anti-dematin antibodies and anti-ankyrin monoclonal antibody showed no obvious abnormalities.
Figure 13B:
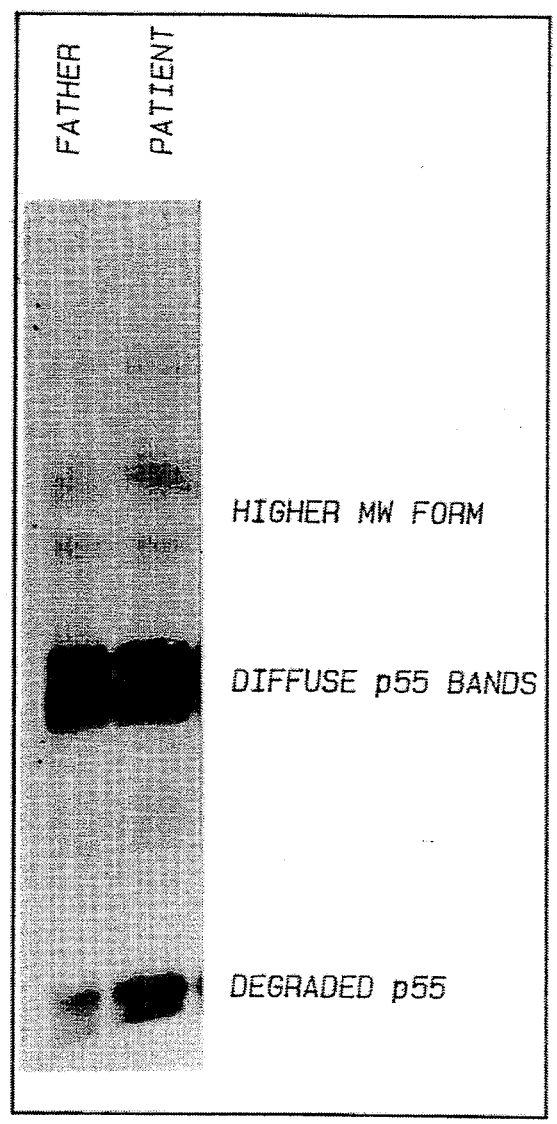

Dyskeratosis congenita (DC) is a recessive disorder which causes dermatological abnormalities, bone marrow hypofunction and a predisposition to neoplasia in early adult life. It has been mapped in the majority (80–90%) of patients to the X chromosome. The locus of DC corresponds with the region to which p55 has been mapped, and there was thus sufficient reason to examine DC patients for abnormalities in p55. When erythrocyte samples taken from a patient and his asymptomatic father were subjected to the p55 Western blot assay, significant anomalies in the migration of p55 were observed. As compared to the normal p55 protein band, several higher molecular weight protein bands and a broad lower molecular weight region of significantly degraded p55 protein were detected by the anti-p55 antibody (FIGS. 13(A) and (B)). Controls using anti-4.1, anti-dematin and monoclonal anti-ankyrin (not shown) revealed no obvious abnormalities in these patients. These results suggest that in DC patients, p55 is synthesized, processed, and/or degraded in an abnormal form. Hence, the p55 Western blot test appears useful in diagnosing this hereditary condition. In both this and the previous case, a diagnostic assay kit can comprise some combination of anti-p55 antibody (monoclonal or polyclonal), reagents for solubilizing and electrophoretically resolving tissue proteins from the patient, reagents for performing the incubation steps, an assay protocol and guidelines for diagnostic interpretation of results.

It will be appreciated that assays for p55, either immunoassays using anti-p55 antibodies or hybridization assays utilizing p55 complementary oligonucleotide probes (described below), are potentially useful in prenatal diagnosis where there is an established risk. Given that the p55 locus is on the X chromosome, it is highly likely that it is linked with at least one of the 18 (estimated) X-linked hereditary disorders mapped to this specific X chromosome region, and possibly more. Diagnostic tests can be utilized in which cell or tissue samples are prepared for PCR amplification of nucleotide sequences hybridizing with p55 cDNA or RNA probes.

Muscular Dystrophies

One form of muscular dystrophy, Emery-Dreifuss muscular dystrophy (EDmd) has been likewise mapped to the region of the X chromosome near where the p55 gene is located. The basic defect in EDmd has not yet been established, but may involve a defect in one or more plasma membrane proteins as is the case with dystrophin, which is responsible for Duchenne muscular dystrophy. Several candidate proteins have been identified in the plasma membrane of muscle cells, which are of similar molecular weight to p55. Once these proteins have been identified, a potential role for p55 in EDmd and other muscular dystrophies may be established.

Hybridization Assays

A mutation or defect in p55 may ultimately be translated into an effect on signal transduction pathways, tissue proliferation and metastasis via the ras pathway. Detection of such a mutation or defect in either the p55 gene or protein would thus provide a useful diagnostic approach for predisposition to cancers of various types. The above-described immunoassays are particularly useful in this context. Hybridization assays utilizing p55 oligonucleotide probes also offer a suitable method for genetic testing for such predisposition, and would be applicable to both prenatal and postnatal cases. By way of illustration, cell or tissue samples can be prepared for PCR amplification of nucleotide sequences hybridizing with p55 cDNA probes.

Probes have already been developed to amplify the following four selected domains of p55:
Domain 1: unidentified domain amino acid residues 3 to 164
Domain 2: unidentified domain amino acid residues 3 to 251
Domain 3: SH3 motif and guanylate kinase domain amino acid residues 164 to 466
Domain 4: guanylate kinase domain amino acid residues 249 to 466

Generally oligonucleotide probes, 15 to 18 nucleic acids in length, with flanking regions on each end were used to ampllify their respective p55 domains using standard PCR techniques. Amplified product was subcloned with prokaryotic expression vectors in order to express peptide/protein corresponding to their domain.

GMP/GDP Conversion by p55

The p55 protein contains a guanylate kinase domain which has been shown to possess enzymatic activity. It is known that the in vivo activity of ras oncoproteins is modulated by the guanine nucleotide balance: a high GTP/GDP ratio activates ras and promotes tumorigenesis. By converting GMP to GDP in vivo, p55 may act to downregulate the ras oncoprotein, thus exerting tumor-suppressive effects in keeping with its presumed sequence-related function. The administration of p55 or its functional equivalent may thus be useful in such intracellular catalyses for downregulation and modulation of tissue proliferation. Furthermore, p55 appears to bind a 21,000 molecular weight protein in vivo (data not shown), whose identity has not yet been established; should this protein turn out to be the 21 kDa ras oncoprotein itself, the mechanism whereby the activity of ras oncoprotein is suppressed by p55 would be clear. Both ras oncoprotein and p55 are palmitoylated peripheral plasma membrane proteins, further suggesting their close association on the membrane.

Those skilled in the art will appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the Figures, specification and following claims.

REFERENCES CITED

1. Siegel, D. L. & Branton, D. (1985) *J. Cell Biol.* 100, 775–785.
2. Husain-Chishti, A., Levin, A. & Branton, D., (1988) *Nature* (London) 334, 718–721.
3. Husain-Chishti, A., Faquin, W., Wu, C. -C. & Branton, D. (1989) *J. Biol. Chem.* 264, 8985–8991.
4. Grosveld, G. (1990) in *Acute Lymphoblastic Leukemia*, eds. Gale, R. F. & Hoelzer, D. (Liss, New York), pp.15–27.
5. Hoffman, F. M., Fresco, L. D., Hoffman-Falk, H. & Shilo, B. -Z (1983) *Cell* 35, 393–401.
6. Pawson, T. (1988) *Oncogene* 3, 491–495.
7. Drubin, D. G., Mulholland, J., Zhimin, Z. & Botstein, D. (1990) *Nature* (London) 343, 288–290
8. Stahl, M. L., Ferenz, C. R., Kelleher, K. L., Kriz, R. W. & Knopf, J. L. (1988) *Nature* (London) 332, 269–272.
9. Jung, G., Korn, E. D. & Hammer, J. A. (1987) *Proc. Natl. Acad. Sci. USA* 84, 6720–6724.

10. Jung, G., Saxe, C. L., Kimmel, A. R. & Hammer, J. A. (1989) *Proc. Natl. Acad. Sci* USA 86, 6186–6190.
11. Ruth, P., Rohrstein, A., Biel, M., Bosse, E., Regulla, S., Meyer, H. E., Flockerzi, V. & Hoffman, F. (1990) *Science* 245, 1115–1118.
12. Leto, T. L., Lomax, K. J., Volpp, B. D., Nunoi, H., Sechler, J. M. G., Nauseef, W. M., Clark, R. A., Gallin, J. I. & Malech, H. L. (1990) *Science* 248, 727–730.
13. Vogel, U. S., Dixon, R. A. F., Scaber, M. D., Diehi, R. E., Marshall, M. S., Scholnick, E. M., Sigal, I. S. & Gibbs, J. B. (1988) *Nature* (London) 335, 90–93.
14. Franz, W. M., Berger, P. & Wang, Y. J. (1989) *EMBO J.* 8, 137–147.
15. Jackson, P. & Baltimore, D. (1989) *EMBO J.* 8, 449–456.
16. Martinez, R., Mathey-Prevot, B., Bernards, A. & Baltimore, D. (1987) *Science* 237, 411–415.
17. Sato, K., Miki, S., Tacibana, H., Hayashi, F., Aklyama, T. & Fukami, Y. (1990) *Biochem. Biophys. Res. Commun.* 171, 1152–1159.
18. Huynh, T. V., Young, R. A. & Davis, R. W. (1985) in *DNA Cloning: A Practical Approach*, ed. Glover, D. M. (IRL, Oxford), Vol. 1, pp49–78.
19. Sambrook, J., Fritsch, E. F. & Maniatis, T. (1989) *Molecular Cloning: A Laboratory Manual* (Cold Spring Harbor Lab., Cold Spring Harbor, N.Y.), 2nd Ed.
20. Sanger, F., Nicklen, S. & Coulson, A. R. (1977) *Proc. Natl. Acad. Sci. USA* 74, 5463–5467; Pharmacia).
21. Goosens, M. & Kan, Y. W. (1981) *Methods Enzymol.* 76, 805–817.
22. Husain-Chishti, A. & Branton, D. (1986) *Anal. Biochem.* 155, 206–211.
23. Jahn, R., Schiebler, W. & Greengard, P. (1984) *Proc. Natl. Acad. Sci. USA* 81, 1684–1687.
24. Maretzki, D., Mariani, M. & Lutz, H. U. (1990) *FEBS Lett.* 259, 305–310.
25. Golden, A., Nemeth, S. P. & Brugge, J. S. (1986) *Proc. Natl. Acad. Sci. USA* 83. 852–856.
26. Kozak, M. (1984) *Nucleic Acids Res.* 12, 857–871.
27. Kyte, J. & Doolittle, R. F. (1982) *J. Mol. Biol.* 157, 105–132.
28. Chou, P. Y. & Fasman, G. D. (1974) *Biochemistry* 13, 222–245.
29. Hanspal, M. & Palek, J. (1987) *J. Cell Biol.* 105, 1417–1424.
30. Bianchi Scarra, G. L., Romani, M., Covielo, D. A., Garre, C., Ravazzolo, R., Vidali, G. & Ajmar, F. (1986) *Cancer Res.* 46, 6327–6332.
31. Pearson, W. R. & Lipman, D. J. (1988) *Proc. Natl. Acad. Sci USA* 85, 2444–2448.
32. Mayer, B. J., Hamaguchi, M. & Hanafusa, H. (1988) *Nature* (London) 332, 272–275.
33. Lehto, V. P., Wasenius, V. -M., Salven, P. & Saraste, M. (1988) *Nature* (London) 334, 388.
34. Dubreuil, R. R., Byers, T. J., Sillman, A. L., Bar-Zvi, D., Goldstein, L. S. B. & Branton, D. (1989) *J. Cell Biol.* 109, 2197–2205.
35. Sahr. K. E., Laurila, P., Scarpa, A. L., Coupal, E., Leto, T. L., Linnebach, A. J., Speicher, D. W., Marchesi, V. T., Curtis, P. J. & Forget, B. G. (1990) *J. Biol. Chem.* 265, 4434–4443.
36. Tyler, J. M., Hargreaves, W. R. & Branton, D. (1979) *Proc. Natl. Acad. Sci. USA* 76, 5192–5196.
37. Bennett, V. (1989) *Biochim, Biophys. Acta* 988, 107–121.
38. Staufenbiel, M. & Lazarides, E. (1986) *Proc. Natl. Acad. Sci USA* 83, 318–322.
39. de Vetten, M. P. & Agre, P. (1988) *J. Biol. Chem.* 263, 18193–18196.
40. Faquin, W. C., Husain-Chishti, A. & Branton, D. (1990) *Eur. J. Cell Biol.* 53, 48–55.
41. Korsgren, C. & Cohen, C. M. (1986) *J. Biol-Chem.* 261, 5536–5543.
42. Schmidt, M. F. G. (1989) *Biochim. Biophys. Acta* 988, 411–426.
43. Ruff, P., Speicher, D. W. and Chishti, A. H. (1991) *Proc. Natl. Acad. Sci. (USA)* 88, 6595–6599.
44. Koch, C. A., Anderson, D., Moran, M. F. Ellis, C., and Pawson, T. (1991) *Science* 52 668–674.
45. Woods, D. F. and Bryant, P. J. (1991) *Cell* 66, 451–464.
46. Hall, S. W., and Kuhn, H. (1986) *Eur. J. Biochem.* 161, 551–556.
47. Whitman, M., Downes, C. P., Keeler, M., Keller, T., and Cantley, L. (1988) *Nature* 332, 644–646.
48. Agarwal, K. C., Miech, R. P., and Parks, R. E. (1978) *Methods Enzymol.* 51, 483–490.
49. Bruns, G., Stroll, H., Veldman, G. M., Latt, S. A. and Floros, J. (1987) *Human Genetics* 76, 58–62.
50. Bryant, P. J., and Woods, D. F. (1992) *Cell* 68, 621–622.
51. Goebl, M. G. (1992) *TIBS* 17, 99.
52. Geobel, S. J., Johnson, G. P., Perkus, M. E., Davis, S. W., Winslow, J. P., and Paoletti, E. (1990) *Virology* 179, 247–266.
53. Delaunay, J., Alloisio, N., Morle. L., and Pothier, B. (1990) *Molec. Aspects Med.* 11, 161–241 (review).
54. Marshall, C. J. (1991) *Cell* 64, 313–326.
55. Berger, A., Schlitz, E., And Schulz, G. E. (1989) *Eur. J. Biochem.* 184, 433–443.
56. Hall, A. (1990) *Cell* 61, 921–923.
57. Hancock. J. F., Magee, A. I., Childs, J. E. and Marshall C. J. (1989) *Cell* 57, 1167–1177.
58. Sherley, J. L. (1991) *J. Biol Chem.* 266, 24815–24828.
59. Ikeda, K., Kikuchi, A., Takai, Y. (1988) *Biochem. Biophys. Res. Commun.* 156, 889–897.
60. McKusick, V. A. (1990) *Mendelian Inheritance in Man*: 9th Edition, Johns Hopkins University Press.
61. Metzenberg, A. B., and Gitschier, J. (1992) *Human Molecular Genetics* 1, 97–101.
62. Connor, J. M., Gatherer, D., Gray, F. C., Pirrit, L. A., and Affara, N. A. (1986) *Human Genetics* 72, 348–351.
63. Huang, X., and Miller, W. (1991) *Adv. Appl. Math.* 12, 373–381.
64. Bruns, G. A. P., Mintz, B. J., Leary, A. C., Regina, V. M., and Gerald, P. S. (1979) *Biochemical Genetics* 17, 1031–1059.
65. Latt, S. A., Willard, H. F., and Gerald, P. S. (1976) *Chromosoma* 57, 135–153.
66. Towbin, H., Gordon J., and Staehelin, T. P (1979) 76, 4350–4354.
67. Hartel-Schenk, S. and Agre, P. (1990) *J. Cell Biol.*, Abstract No. 1800.
68. Harlow, E. et al (1988), *Antibodies: A Laboratory Manual*: Cold Spring Harbor, N.Y.

All publications cited herein are incorporated by reference.

( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2000 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 115..1512
        ( C ) IDENTIFICATION METHOD: experimental
        ( D ) OTHER INFORMATION: /product="protein"
            / evidence=EXPERIMENTAL
            / note="Polyadenylation consensus sequence is at
            nucleic acid residues 1982-1987. Amino acid
            residues 165- 233 represent the SH-3 motif."

( x ) PUBLICATION INFORMATION:
        ( A ) AUTHORS: Andrabi, Khurshid
            Rana, Ajay
            Keeler, Marilyn
            Maalouf, George
            Bruns, Gail
            Chishti, Athar
        ( B ) TITLE: Human erythroid p55: Homolog of Drosophilia
            tumor suppressor factor is highly conserved
            X-linked gene product with guanylate kinase
            activity
        ( C ) JOURNAL: J. Biol. Chem.
        ( G ) DATE: 1992

( x ) PUBLICATION INFORMATION:
        ( A ) AUTHORS: Ruff, Paul
            Speicher, David W.
            Husain- Chishti, A.
        ( B ) TITLE: Molecular identification of a major
            palmitoylated erythrocyte membrane protein
            containing the src homology 3 motif
        ( C ) JOURNAL: Proc. Natl. Acad. Sci. U.S.A.
        ( D ) VOLUME: 88
        ( F ) PAGES: 6595-6599
        ( G ) DATE: August-1991
        ( K ) RELEVANT RESIDUES IN SEQ ID NO:1: FROM 1 TO 2000

( x ) PUBLICATION INFORMATION:
        ( A ) AUTHORS: Husain-Chishti, Athar
            Faquin, William
            Wu, Chi- Chih
            Branton, Daniel
        ( B ) TITLE: Purification of Erthrocyte of Dematin
           ( P r o t e i n  4 . 9 ) Reveals an Endogenous Protein Kinase
            That Modulates Actin-bundling Activity
        ( C ) JOURNAL: J. Biol. Chem.
        ( D ) VOLUME: 264
        ( E ) ISSUE: 15
        ( F ) PAGES: 8985-8991
        ( G ) DATE: 5-25-1989

( x i ) SEQUENCE DESCRIPTION: SEQ ID NO:1:

```
CCCCCCCCCC CAGCCGCACC GCGTCTCCCG CCTTCTCCGC AGCCCCGCAG GCCCCGGGCC           60

CTGTCATTCC CAGCGCTGCC CTGTCTTGCG TTCCAGTGTT CCAGCTTCTG CGAG ATG           117
                                                              Met
                                                              1

ACC CTC AAG GCG AGC GAG GGC GAG AGT GGG GGC AGC ATG CAC ACG GCG           165
Thr Leu Lys Ala Ser Glu Gly Glu Ser Gly Gly Ser Met His Thr Ala
        5                   10                  15

CTC TCC GAC CTC TAC CTG GAG CAT TTG CTG CAG AAG CGT AGT CGG CCA           213
Leu Ser Asp Leu Tyr Leu Glu His Leu Leu Gln Lys Arg Ser Arg Pro
```

|  |  |  |  |  |  |  |  |  |  |  |  |  |  |  |  |
|---|---|---|---|---|---|---|---|---|---|---|---|---|---|---|---|
|  | 20 |  |  |  | 25 |  |  |  |  | 30 |  |  |  |  |  |
| GAG | GCT | GTA | TCG | CAT | CCA | TTG | AAT | ACT | GTG | ACC | GAG | GAC | ATG | TAC | ACC | 261 |
| Glu | Ala | Val | Ser | His | Pro | Leu | Asn | Thr | Val | Thr | Glu | Asp | Met | Tyr | Thr |  |
|  | 35 |  |  |  | 40 |  |  |  |  | 45 |  |  |  |  |  |  |
| AAC | GGG | TCT | CCT | GCC | CCA | GGT | AGC | CCT | GCC | CAG | GTC | AAG | GGA | CAG | GAG | 309 |
| Asn | Gly | Ser | Pro | Ala | Pro | Gly | Ser | Pro | Ala | Gln | Val | Lys | Gly | Gln | Glu |  |
| 50 |  |  |  |  | 55 |  |  |  |  | 60 |  |  |  |  | 65 |  |
| GTG | CGG | AAA | GTG | CGA | CTC | ATA | CAG | TTT | GAG | AAG | GTC | ACA | GAA | GAG | CCC | 357 |
| Val | Arg | Lys | Val | Arg | Leu | Ile | Gln | Phe | Glu | Lys | Val | Thr | Glu | Glu | Pro |  |
|  |  |  |  | 70 |  |  |  |  | 75 |  |  |  |  | 80 |  |  |
| ATG | GGA | ATC | ACG | CTG | AAG | CTG | AAT | GAA | AAA | CAG | TCC | TGT | ACG | GTG | GCC | 405 |
| Met | Gly | Ile | Thr | Leu | Lys | Leu | Asn | Glu | Lys | Gln | Ser | Cys | Thr | Val | Ala |  |
|  |  |  |  | 85 |  |  |  |  | 90 |  |  |  |  | 95 |  |  |
| AGA | ATT | CTT | CAT | GGT | GGC | ATG | ATC | CAT | AGA | CAA | GGC | TCC | CTT | CAC | GTG | 453 |
| Arg | Ile | Leu | His | Gly | Gly | Met | Ile | His | Arg | Gln | Gly | Ser | Leu | His | Val |  |
|  |  |  | 100 |  |  |  |  | 105 |  |  |  |  | 110 |  |  |  |
| GGG | GAT | GAG | ATC | CTA | GAA | ATC | AAT | GGC | ACA | AAT | GTG | ACA | AAT | CAT | TCA | 501 |
| Gly | Asp | Glu | Ile | Leu | Glu | Ile | Asn | Gly | Thr | Asn | Val | Thr | Asn | His | Ser |  |
|  | 115 |  |  |  |  | 120 |  |  |  |  | 125 |  |  |  |  |  |
| GTG | GAT | CAG | CTG | CAG | AAG | GCG | ATG | AAA | GAA | ACC | AAA | GGA | ATG | ATC | TCA | 549 |
| Val | Asp | Gln | Leu | Gln | Lys | Ala | Met | Lys | Glu | Thr | Lys | Gly | Met | Ile | Ser |  |
| 130 |  |  |  |  | 135 |  |  |  |  | 140 |  |  |  |  | 145 |  |
| TTA | AAA | GTA | ATT | CCC | AAC | CAG | CAA | AGC | CGT | CTT | CCT | GCA | CTA | CAG | ATG | 597 |
| Leu | Lys | Val | Ile | Pro | Asn | Gln | Gln | Ser | Arg | Leu | Pro | Ala | Leu | Gln | Met |  |
|  |  |  |  | 150 |  |  |  |  | 155 |  |  |  |  | 160 |  |  |
| TTC | ATG | AGA | GCG | CAG | TTT | GAC | TAT | GAT | CCC | AAA | AAG | GAC | AAT | CTG | ATC | 645 |
| Phe | Met | Arg | Ala | Gln | Phe | Asp | Tyr | Asp | Pro | Lys | Lys | Asp | Asn | Leu | Ile |  |
|  |  |  | 165 |  |  |  |  | 170 |  |  |  |  | 175 |  |  |  |
| CCT | TGC | AAG | GAG | GCG | GGA | CTG | AAG | TTT | GCT | ACT | GGG | GAC | ATT | ATC | CAG | 693 |
| Pro | Cys | Lys | Glu | Ala | Gly | Leu | Lys | Phe | Ala | Thr | Gly | Asp | Ile | Ile | Gln |  |
|  |  | 180 |  |  |  |  | 185 |  |  |  |  | 190 |  |  |  |  |
| ATT | ATC | AAC | AAG | GAT | GAC | AGC | AAT | TGG | TGG | CAG | GGA | CGG | GTG | GAA | GGC | 741 |
| Ile | Ile | Asn | Lys | Asp | Asp | Ser | Asn | Trp | Trp | Gln | Gly | Arg | Val | Glu | Gly |  |
|  | 195 |  |  |  |  | 200 |  |  |  |  | 205 |  |  |  |  |  |
| TCC | TCC | AAG | GAG | TCA | GCA | GGA | TTG | ATC | CCT | TCC | CCT | GAG | CTG | CAG | GAA | 789 |
| Ser | Ser | Lys | Glu | Ser | Ala | Gly | Leu | Ile | Pro | Ser | Pro | Glu | Leu | Gln | Glu |  |
| 210 |  |  |  |  | 215 |  |  |  |  | 220 |  |  |  |  | 225 |  |
| TGG | CGA | GTG | GCA | AGT | ATG | GCT | CAG | TCA | GCT | CCT | AGC | GAA | GCC | CCG | AGC | 837 |
| Trp | Arg | Val | Ala | Ser | Met | Ala | Gln | Ser | Ala | Pro | Ser | Glu | Ala | Pro | Ser |  |
|  |  |  |  | 230 |  |  |  |  | 235 |  |  |  |  | 240 |  |  |
| TGC | AGT | CCC | TTT | GGG | AAG | AAG | AAG | AAG | TAC | AAA | GAC | AAA | TAT | CTG | GCC | 885 |
| Cys | Ser | Pro | Phe | Gly | Lys | Lys | Lys | Lys | Tyr | Lys | Asp | Lys | Tyr | Leu | Ala |  |
|  |  |  | 245 |  |  |  |  | 250 |  |  |  |  | 255 |  |  |  |
| AAG | CAC | AGC | TCG | ATT | TTT | GAT | CAG | TTG | GAT | GTT | GTT | TCC | TAC | GAG | GAA | 933 |
| Lys | His | Ser | Ser | Ile | Phe | Asp | Gln | Leu | Asp | Val | Val | Ser | Tyr | Glu | Glu |  |
|  |  | 260 |  |  |  |  | 265 |  |  |  |  | 270 |  |  |  |  |
| GTC | GTT | CGG | CTC | CCT | GCA | TTC | AAG | AGG | AAG | ACC | CTG | GTG | CTG | ATC | GGA | 981 |
| Val | Val | Arg | Leu | Pro | Ala | Phe | Lys | Arg | Lys | Thr | Leu | Val | Leu | Ile | Gly |  |
|  | 275 |  |  |  |  | 280 |  |  |  |  | 285 |  |  |  |  |  |
| GCC | AGT | GGG | GTG | GGT | CGC | AGC | CAC | ATT | AAG | AAT | GCC | CTG | CTC | AGC | CAG | 1029 |
| Ala | Ser | Gly | Val | Gly | Arg | Ser | His | Ile | Lys | Asn | Ala | Leu | Leu | Ser | Gln |  |
| 290 |  |  |  |  | 295 |  |  |  |  | 300 |  |  |  |  | 305 |  |
| AAT | CCG | GAG | AAG | TTT | GTG | TAC | CCT | GTC | CCA | TAT | ACA | ACA | CGG | CCG | CCA | 1077 |
| Asn | Pro | Glu | Lys | Phe | Val | Tyr | Pro | Val | Pro | Tyr | Thr | Thr | Arg | Pro | Pro |  |
|  |  |  |  | 310 |  |  |  |  | 315 |  |  |  |  | 320 |  |  |
| AGG | AAG | AGT | GAG | GAA | GAT | GGG | AAG | GAG | TAC | CAC | TTT | ATC | TCA | ACG | GAG | 1125 |
| Arg | Lys | Ser | Glu | Glu | Asp | Gly | Lys | Glu | Tyr | His | Phe | Ile | Ser | Thr | Glu |  |
|  |  |  | 325 |  |  |  |  | 330 |  |  |  |  | 335 |  |  |  |
| GAG | ATG | ACG | AGG | AAC | ATC | TCT | GCC | AAT | GAG | TTC | TTG | GAG | TTT | GGC | AGC | 1173 |
| Glu | Met | Thr | Arg | Asn | Ile | Ser | Ala | Asn | Glu | Phe | Leu | Glu | Phe | Gly | Ser |  |
|  |  | 340 |  |  |  |  | 345 |  |  |  |  | 350 |  |  |  |  |

| | | | | | | | | | | | | | | | | |
|---|---|---|---|---|---|---|---|---|---|---|---|---|---|---|---|---|
| TAC | CAA | GGC | AAC | ATG | TTT | GGC | ACC | AAA | TTT | GAA | ACA | GTG | CAC | CAG | ATC | 1221 |
| Tyr | Gln | Gly | Asn | Met | Phe | Gly | Thr | Lys | Phe | Glu | Thr | Val | His | Gln | Ile | |
| | 355 | | | | 360 | | | | | 365 | | | | | | |
| CAT | AAG | CAG | AAC | AAG | ATT | GCC | ATC | CTT | GAC | ATT | GAG | CCC | CAG | ACC | CTG | 1269 |
| His | Lys | Gln | Asn | Lys | Ile | Ala | Ile | Leu | Asp | Ile | Glu | Pro | Gln | Thr | Leu | |
| 370 | | | | 375 | | | | | 380 | | | | | | 385 | |
| AAA | ATT | GTT | CGG | ACA | GCA | GAA | CTT | TCG | CCT | TTC | ATT | GTG | TTC | ATT | GCA | 1317 |
| Lys | Ile | Val | Arg | Thr | Ala | Glu | Leu | Ser | Pro | Phe | Ile | Val | Phe | Ile | Ala | |
| | | | 390 | | | | | 395 | | | | | | 400 | | |
| CCT | ACT | GAC | CAG | GGC | ACT | CAG | ACA | GAA | GCC | CTG | CAG | CAG | CTG | CAG | AAG | 1365 |
| Pro | Thr | Asp | Gln | Gly | Thr | Gln | Thr | Glu | Ala | Leu | Gln | Gln | Leu | Gln | Lys | |
| | | 405 | | | | 410 | | | | | 415 | | | | | |
| GAC | TCT | GAG | GCC | ATC | CGC | AGC | CAG | TAC | GCT | CAC | TAC | TTT | GAC | CTC | TCA | 1413 |
| Asp | Ser | Glu | Ala | Ile | Arg | Ser | Gln | Tyr | Ala | His | Tyr | Phe | Asp | Leu | Ser | |
| | 420 | | | | | 425 | | | | | 430 | | | | | |
| CTG | GTC | AAT | AAT | GGT | GTT | GAT | GAA | ACC | CTT | AAG | AAA | TTA | CAA | GAA | GCC | 1461 |
| Leu | Val | Asn | Asn | Gly | Val | Asp | Glu | Thr | Leu | Lys | Lys | Leu | Gln | Glu | Ala | |
| 435 | | | | | 440 | | | | | 445 | | | | | | |
| TTC | GAC | CAA | GCG | TGC | AGT | TCT | CCA | CAG | TGG | GTG | CCT | GTC | TCC | TGG | GTT | 1509 |
| Phe | Asp | Gln | Ala | Cys | Ser | Ser | Pro | Gln | Trp | Val | Pro | Val | Ser | Trp | Val | |
| 450 | | | | | 455 | | | | 460 | | | | | | 465 | |
| TAC | TAAGCTTGTA | GAATGGGGGA | ACCCACTGTA | TGCCCCTCTC | CAGCATTTGG | | | | | | | | | | | 1562 |
| Tyr | | | | | | | | | | | | | | | | |

| | | | | | |
|---|---|---|---|---|---|
| AATTCCACCC | GCCTTGCTTT | AAGACAAACA | GGGCTGCTCC | AACTAGTTTT | GTGTCAGCTT | 1622 |
| CCAGCTCTCT | GCAGCTATCC | TAATTCAGCC | AGTAAGGTTC | AGTCTTCTTG | CTCAGGCTCC | 1682 |
| TGAAGGGTTG | ATTCTCCTGA | TAGATGGGGC | CCCACTGATC | TGGATTTGAA | AAGGATTTCT | 1742 |
| AGAAATTGGG | GGTAAGAAGT | ACTACCAAAA | TGTAACTGCT | AATCAAGGGT | GATGCACAGC | 1802 |
| AAAAGCAATG | GACCCCATCC | CTCTAAAGCC | TGCCCTCCTT | TGCCTTCAAC | TGTATATGCT | 1862 |
| GGGTATTTCA | TTTGTCTTTT | TATTTGGAG | AAAGCGTTTT | TAACTGCAAC | TTTCTATAAT | 1922 |
| GCCAAAATGA | CACATCTGTG | CAATAGAATG | ATGTCTGCTC | TAGGGAAACC | TTCAAAAGCA | 1982 |
| ATAAAAATGC | TGTGTTGG | | | | | 2000 |

( 2 ) INFORMATION FOR SEQ ID NO:2:

( i ) SEQUENCE CHARACTERISTICS:
        ( A ) LENGTH: 466 amino acids
        ( B ) TYPE: amino acid ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Thr | Leu | Lys | Ala | Ser | Glu | Gly | Glu | Ser | Gly | Gly | Ser | Met | His | Thr |
| 1 | | | | 5 | | | | | 10 | | | | | 15 | |
| Ala | Leu | Ser | Asp | Leu | Tyr | Leu | Glu | His | Leu | Leu | Gln | Lys | Arg | Ser | Arg |
| | | | 20 | | | | | 25 | | | | | 30 | | |
| Pro | Glu | Ala | Val | Ser | His | Pro | Leu | Asn | Thr | Val | Thr | Glu | Asp | Met | Tyr |
| | | 35 | | | | | 40 | | | | | 45 | | | |
| Thr | Asn | Gly | Ser | Pro | Ala | Pro | Gly | Ser | Pro | Ala | Gln | Val | Lys | Gly | Gln |
| | 50 | | | | | 55 | | | | | 60 | | | | |
| Glu | Val | Arg | Lys | Val | Arg | Leu | Ile | Gln | Phe | Glu | Lys | Val | Thr | Glu | Glu |
| 65 | | | | | 70 | | | | | 75 | | | | | 80 |
| Pro | Met | Gly | Ile | Thr | Leu | Lys | Leu | Asn | Glu | Lys | Gln | Ser | Cys | Thr | Val |
| | | | | 85 | | | | | 90 | | | | | 95 | |
| Ala | Arg | Ile | Leu | His | Gly | Gly | Met | Ile | His | Arg | Gln | Gly | Ser | Leu | His |
| | | | 100 | | | | | 105 | | | | | 110 | | |
| Val | Gly | Asp | Glu | Ile | Leu | Glu | Ile | Asn | Gly | Thr | Asn | Val | Thr | Asn | His |
| | | 115 | | | | | 120 | | | | | 125 | | | |

-continued

| | | | | | | | | | | | | | |
|---|---|---|---|---|---|---|---|---|---|---|---|---|---|
| Ser | Val 130 | Asp | Gln | Leu | Gln 135 | Lys | Ala | Met | Lys | Glu | Thr 140 | Lys | Gly | Met | Ile |
| Ser 145 | Leu | Lys | Val | Ile | Pro 150 | Asn | Gln | Gln | Ser | Arg 155 | Leu | Pro | Ala | Leu | Gln 160 |
| Met | Phe | Met | Arg | Ala 165 | Gln | Phe | Asp | Tyr | Asp 170 | Pro | Lys | Lys | Asp | Asn 175 | Leu |
| Ile | Pro | Cys | Lys 180 | Glu | Ala | Gly | Leu | Lys 185 | Phe | Ala | Thr | Gly | Asp 190 | Ile | Ile |
| Gln | Ile | Ile 195 | Asn | Lys | Asp | Asp | Ser 200 | Asn | Trp | Trp | Gln | Gly 205 | Arg | Val | Glu |
| Gly | Ser 210 | Ser | Lys | Glu | Ser | Ala 215 | Gly | Leu | Ile | Pro | Ser 220 | Pro | Glu | Leu | Gln |
| Glu 225 | Trp | Arg | Val | Ala | Ser 230 | Met | Ala | Gln | Ser | Ala 235 | Pro | Ser | Glu | Ala | Pro 240 |
| Ser | Cys | Ser | Pro | Phe 245 | Gly | Lys | Lys | Lys | Tyr 250 | Lys | Asp | Lys | Tyr 255 | Leu |
| Ala | Lys | His | Ser 260 | Ser | Ile | Phe | Asp | Gln 265 | Leu | Asp | Val | Val | Ser 270 | Tyr | Glu |
| Glu | Val | Val 275 | Arg | Leu | Pro | Ala | Phe 280 | Lys | Arg | Lys | Thr | Leu 285 | Val | Leu | Ile |
| Gly | Ala 290 | Ser | Gly | Val | Gly | Arg 295 | Ser | His | Ile | Lys | Asn 300 | Ala | Leu | Leu | Ser |
| Gln 305 | Asn | Pro | Glu | Lys | Phe 310 | Val | Tyr | Pro | Val | Pro 315 | Tyr | Thr | Thr | Arg | Pro 320 |
| Pro | Arg | Lys | Ser | Glu 325 | Glu | Asp | Gly | Lys | Glu 330 | Tyr | His | Phe | Ile | Ser 335 | Thr |
| Glu | Glu | Met | Thr 340 | Arg | Asn | Ile | Ser | Ala 345 | Asn | Glu | Phe | Leu | Glu 350 | Phe | Gly |
| Ser | Tyr | Gln 355 | Gly | Asn | Met | Phe | Gly 360 | Thr | Lys | Phe | Glu | Thr 365 | Val | His | Gln |
| Ile | His 370 | Lys | Gln | Asn | Lys | Ile 375 | Ala | Ile | Leu | Asp | Ile 380 | Glu | Pro | Gln | Thr |
| Leu 385 | Lys | Ile | Val | Arg | Thr 390 | Ala | Glu | Leu | Ser | Pro 395 | Phe | Ile | Val | Phe | Ile 400 |
| Ala | Pro | Thr | Asp | Gln 405 | Gly | Thr | Gln | Thr | Glu 410 | Ala | Leu | Gln | Gln | Leu 415 | Gln |
| Lys | Asp | Ser | Glu 420 | Ala | Ile | Arg | Ser | Gln 425 | Tyr | Ala | His | Tyr | Phe 430 | Asp | Leu |
| Ser | Leu | Val 435 | Asn | Asn | Gly | Val | Asp 440 | Glu | Thr | Leu | Lys | Lys 445 | Leu | Gln | Glu |
| Ala | Phe 450 | Asp | Gln | Ala | Cys | Ser 455 | Ser | Pro | Gln | Trp | Val 460 | Pro | Val | Ser | Trp |
| Val 465 | Tyr |

We claim:

1. An isolated nucleic acid encoding the amino acid of SEQ ID NO. 2.
2. An isolated human enythroid p55 transcript encoding the amino acid sequence of SEQ ID NO. 2.
3. An isolated nucleic acid template for the transcript of claim 2.
4. An isolated nucleic acid having a sequence complementary to the sequence of the template of claim 3.
5. An isolated nucleic acid having the sequence of SEQ ID NO. 1.
6. An isolated nucleic acid comprising nucleotides 115 to 1512 of the nucleic acid sequence of claim 5.
7. An isolated nucleic acid having a sequence fully complementary to the sequence of claim 5.
8. An isolated nucleic acid having a sequence fully complementary to the sequence of claim 6.
9. An isolated oligonucleotide comprising at least eighteen nucleotides of the nucleic acid of claim 5 which will hybridize to the nucleic acid of claim 7.
10. An isolated oligonucleotide having a sequence fully complementary to the sequence of the oligonucleotide of claim 9.
11. An isolated transcript of the nucleic acid of SEQ ID NO. 1.

* * * * *